United States Patent [19]
Goodwin et al.

[11] Patent Number: 5,569,585
[45] Date of Patent: Oct. 29, 1996

[54] IN VITRO ASSAY MEASURING DEGREE OF ACTIVATION OF IMMUNE CELLS

[75] Inventors: Joseph J. Goodwin, Waltham; Barry I. Caplan, Newton; Bruce P. Babbitt, North Easton, all of Mass.

[73] Assignee: Cellcor, Inc., Newton, Mass.

[21] Appl. No.: 214,400

[22] Filed: Mar. 16, 1994

Related U.S. Application Data

[63] Continuation-in-part of Ser. No. 30,607, Mar. 12, 1993, abandoned, which is a continuation-in-part of Ser. No. 963,846, Oct. 21, 1996, abandoned.

[51] Int. Cl.⁶ .................. C12Q 1/02; C12Q 1/68
[52] U.S. Cl. ............. 435/6; 424/9.2; 424/93.71; 435/7.24; 435/29; 436/63
[58] Field of Search ............... 435/6, 7.24, 29; 436/63; 424/278.1, 93.71, 534, 9.2

[56] References Cited

U.S. PATENT DOCUMENTS

| | | | |
|---|---|---|---|
| 4,778,750 | 10/1988 | Gottlieb | 435/5 |
| 5,180,662 | 1/1993 | Sitkovsky | 435/7.24 |
| 5,296,353 | 3/1994 | Ochoa et al. | 435/7.24 |

FOREIGN PATENT DOCUMENTS

WO88/02774  4/1988  WIPO.

OTHER PUBLICATIONS

M. Schrezenmeier et al, Europ. Journ. Immunol., 15, 1019–1024, 1985.
B. Babbit et al, Jour. Urol., 149, (4 Suppl.), 463A, 1993.
B. Babbit et al, Jour Cell. Biochem., Suppl 0, (17 Part D), 130, 1993.
B. Babbit et al, Proc. Amer. Assoc. Cancer Research, Ann. Meet., 34, (0), 443, 1993.
Abb, J., et al., "Lymphocyte Activation by the Tumor-Promoting Agent 12-O-Tetradecanoylphorbol-13-Acetate (TPA)", 1979 *J. Immunology*, 122:1639–1642.
McCrady, C., et al., "Alteration of Human Lymphokine-activated Killer Cell Activity by Manipulation of Protein Kinase C and Cytosolic $Ca^{2+}$", 1988, *Cancer Research*, 48:635–640.

*Primary Examiner*—David Saunders
*Attorney, Agent, or Firm*—Fish & Richardson P.C.

[57] ABSTRACT

This invention is directed to a method for assaying the degree of activation of immune cells by stimulating non-resting immune cells to activity with an intracellular-acting stimulant and then measuring the activity of the stimulated immune cells. The stimulant that can be used in this invention will effectively stimulate non-resting immune cells to activity, but will not effectively stimulate resting immune cells to activity. The stimulants that can be used in the invention of this assay act directly as activation probes. These stimulants can discern evidence of previous immune cell activation and will therefore effectively stimulate to activity primed immune cells. Since the stimulant discerns previous immune cell activation, the stimulants of this invention will not effectively stimulate to activity resting immune cells. The assay measurements can be used for a variety of evaluations, including correlating in vitro activity of ex vivo activated (EVA) with clinical outcome of the therapy with such cells.

44 Claims, 10 Drawing Sheets

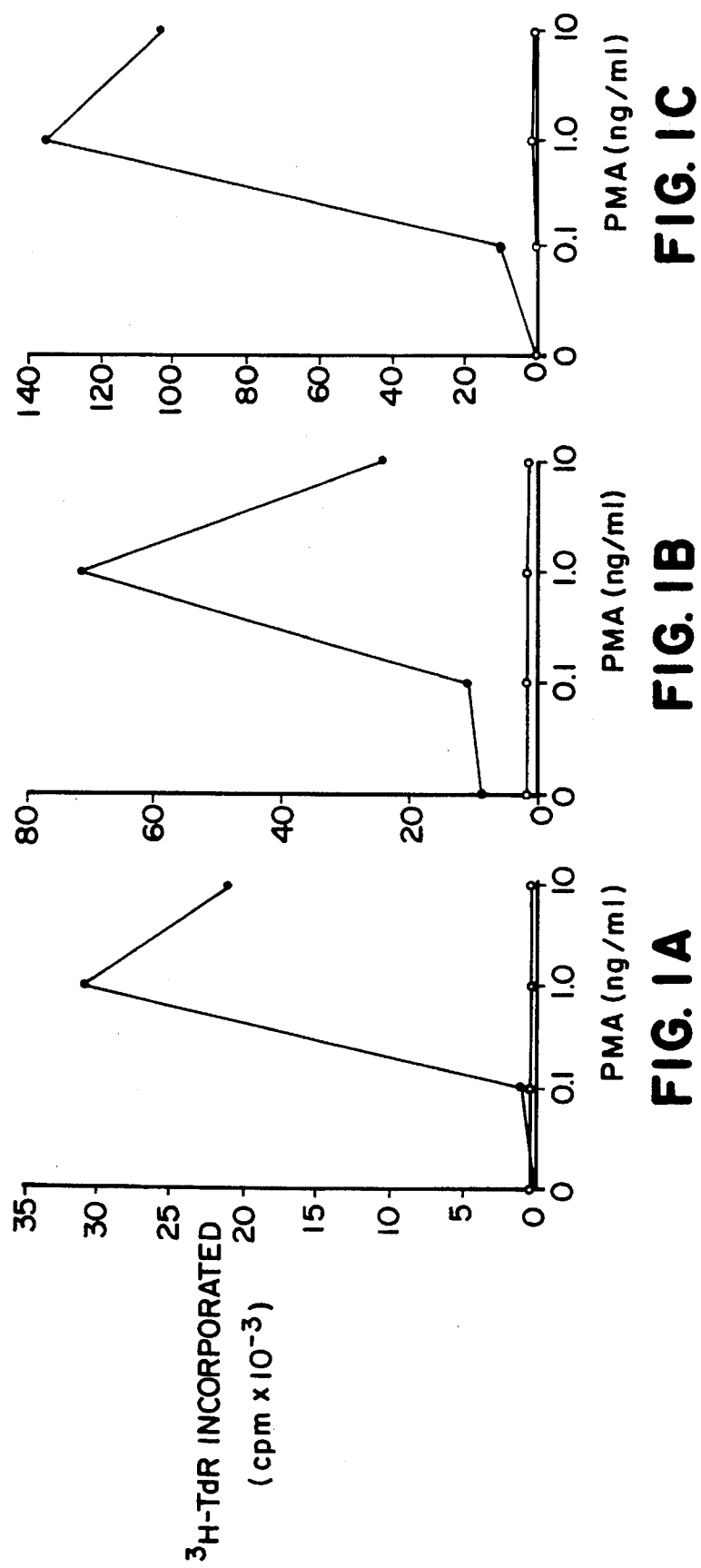

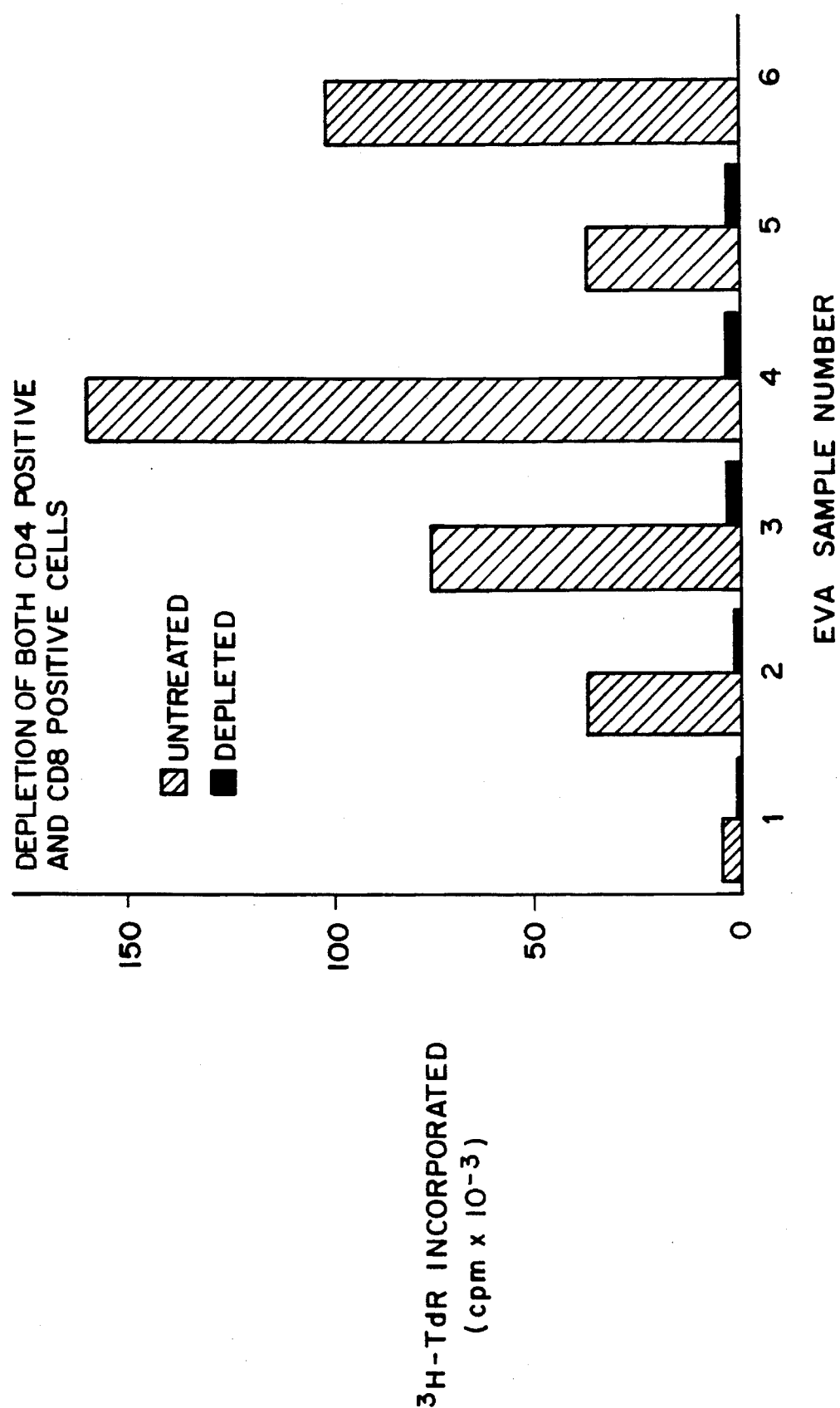

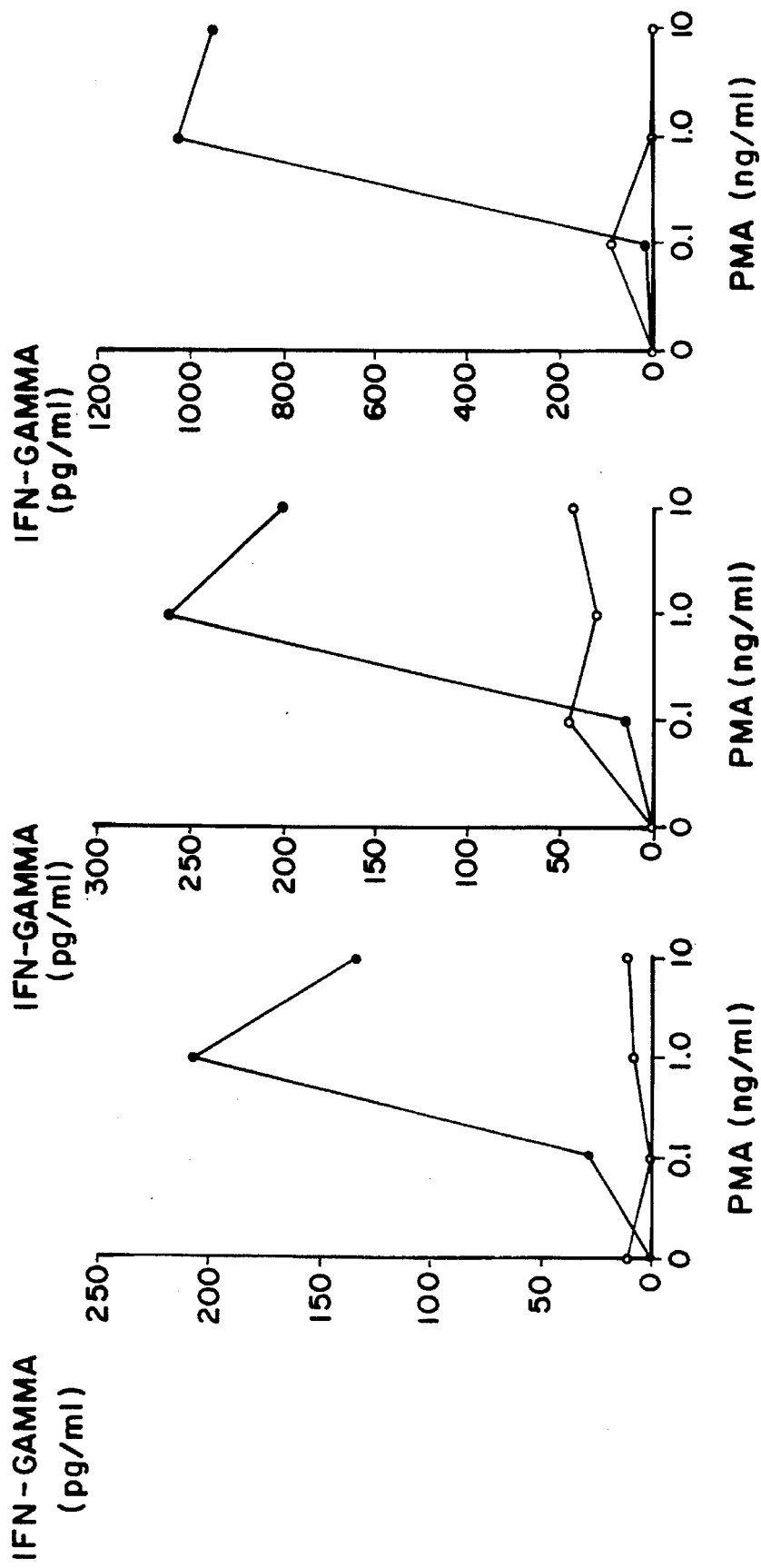

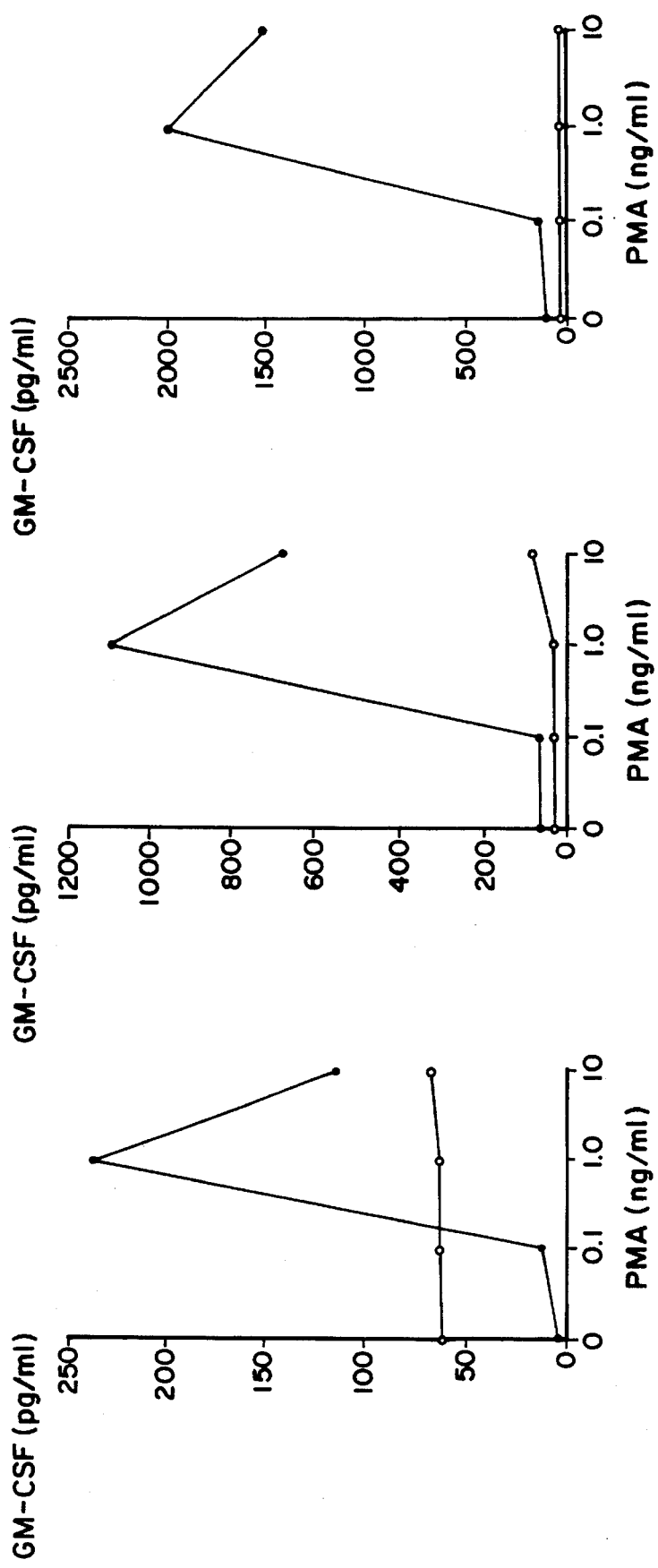

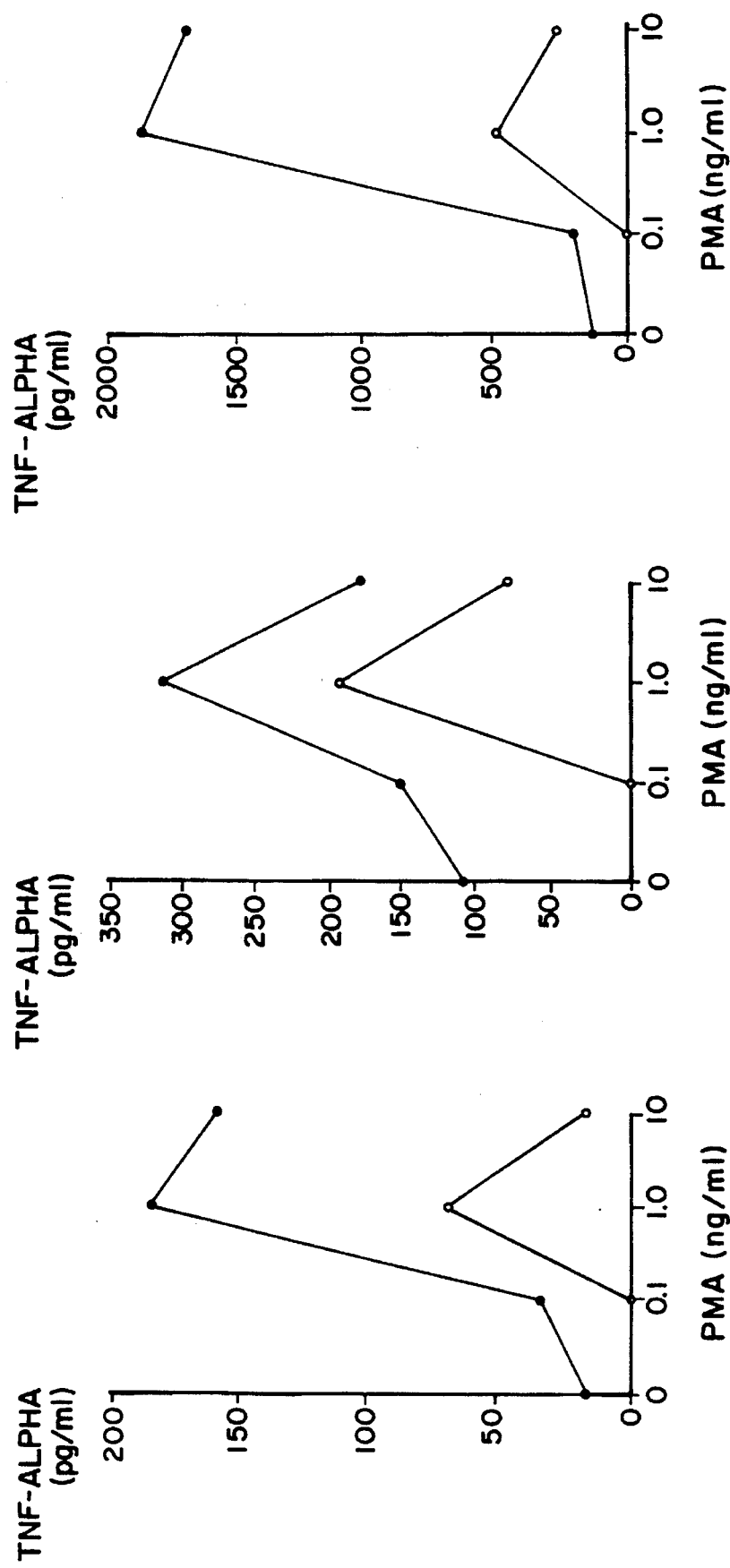

DESCRIPTIVE STATISTICS

|   | MEDIUM | T3CS |
|---|---|---|
| MEAN | 6956.250 | 42734.562 |
| STD. ERROR | 3478.587 | 15623.292 |
| COUNT | 8 | 8 |
| MINIMUM | 195.900 | 1841.300 |
| MAXIMUM | 26650.100 | 110019.300 |

PAIRED t-TEST
HYPOTHESIZED DIFFERENCE AS 0

|   | MEAN DIFFERENCE | DF | t-VALUE | P-VALUE |
|---|---|---|---|---|
| MEDIUM, T3CS | -35778.31 | 7 | -2.86 | .0245 |

ENHANCED PROLIFERATIVE RESPONSES OF EVA CELLS TO IONOMYCIN

IN VITRO ASSAY MEASURING DEGREE OF ACTIVATION OF IMMUNE CELLS

CROSS REFERENCE TO RELATED APPLICATIONS

This application is a continuation-in-part of U.S. patent application Ser. No. 08/030,607, filed Mar. 12, 1993, and now abandoned, which is a continuation-in-part of U.S. patent application Ser. No. 07/963,486, filed Oct. 21, 1992, and now abandoned. Both of the above-referenced applications are incorporated herein by reference.

FIELD OF THE INVENTION

This invention is directed to an in vitro assay for determining the degree of activation of immune cells by stimulating immune cells to activity with a stimulant and then measuring the activity of the immune cells. The stimulant that can be used in this invention will effectively stimulate non-resting immune cells to activity, but will not effectively stimulate resting immune cells to activity. The stimulants that can be used in the invention of this assay act directly as an activation probe. These stimulants can discern evidence of previous immune cell activation and will therefore effectively stimulate to activity non-resting immune cells. Since the stimulant discerns previous immune cell activation, the stimulants of this invention will not effectively stimulate to activity resting immune cells. The assay measurements can be used for a variety of evaluations, including correlating in vitro activity with clinical outcome of the therapy.

BACKGROUND OF THE INVENTION

Adoptive cellular immunotherapy is a treatment that employs biological reagents to effect an immune-mediated response. Currently, most adoptive immunotherapies are autolymphocyte therapies (ALT) directed to treatments using the patient's own immune cells. These therapies involve processing the patient's own lymphocytes to either enhance the immune cell mediated response or to recognize specific antigens or foreign substances in the body, including the cancer cells. The treatments are accomplished by removing the patient's lymphocytes and exposing these cells in vitro to biologics and drugs to activate the immune function of the cells. Once the autologous cells are activated, these ex vivo activated cells are reinfused into the patient to enhance the immune system to treat various forms of cancer, infectious diseases, autoimmune diseases or immune deficiency diseases.

Osband et al., *The Lancet* 335:994–998 (1990), describe an autolymphocyte therapy to treat metastatic renal cell carcinoma (mRCC). In this procedure, an autologous cytokine mixture is prepared using the patient's peripheral blood mononuclear T cells. Then, autologous lymphocytes are stimulated with the autologous cytokine mixture and with various activating agents, such as antibodies against T cell surface antigens. Once the autologous lymphocytes are activated, the cells are reinfused into the patient to enhance the immune response.

Another autolymphocyte therapy in the treatment of kidney cancer is the processing of a cancer patient's natural killer (NK) cells, with interleukin-2 (IL-2). This processing stimulates the immune cells to proliferate. The activated NK cells are then reinfused into the cancer patient, where the infused cells proliferate and mediate an immune response. Feinfeld et al., "Interstitial nephritis in a patient receiving adoptive immunotherapy with recombinant interleukin-2 and lymphokine-activated killer cells," *American Journal of Nephrology* 11:489–492 (1991).

Two additional autolymphocyte therapies are lymphokine-activated killer cell (LAK) therapy and tumor-infiltrating lymphocyte (TIL) therapy. LAK therapy involves the in vitro generation of LAK cells by culturing autologous peripheral blood leukocytes in high concentrations of IL-2. The LAK cells are then reinfused into the cancer patient in a treatment that may also involves infusion of IL-2. Rosenberg and Lotze, "Cancer immunotherapy using interleukin-2 and interleukin-2 activated lymphocytes," *Annual Review of Immunology* 4:681–709 (1986). TIL therapy involves the generation of LAK cells from mononuclear cells originally derived from the inflammatory infiltrating cells present in and around solid tumors, obtained from surgical resection specimens. The rationale for this appropriate is that TILs may be enriched for tumor-specific killer cells. The processed TIL cells are then reinfused into the patient to promote an immune mediated response to the tumor cells. Rosenberg et al., "A new approach to the adoptive immunotherapy of cancer with tumor-infiltrating lymphocytes," *Science* 233:1318–1321 (1986).

An autolymphocyte therapy using tumor cells for the treatment of melanoma involves the in vitro stimulation and culturing of peripheral lymphocytes, or lymph node cells, together with the patient's melanoma cells or with HLA-A region matched allogeneic melanoma. The immune cells are repeatedly stimulated with the tumor cells and IL-2, and then further induced and amplified with phorbol dibutyrate and ionomycin. Darrow et al., "Modulation of In Vitro Autologous Melanoma-Specific Cytotoxic T-Cell Responses by Phorbol Dibutyrate and Ionomycin," *Cellular Immunology* 125:508–517 (1990).

Yet another autolymphocyte therapy is a procedure called autologous bone marrow transplant (BMT) used for treating leukemia, testicular cancer and lymphoma. Bone marrow is removed from the cancer patient prior to chemotherapy. The bone marrow is processed and cryopreserved. Following chemotherapy, the patient then receives the autologous treated bone marrow. R. Champlin and R. P. Gale, "Bone Marrow Transplantation: Its Biology and Role as Treatment for Acute and Chronic Leukemias; in *Normal and Neoplastic Blood Cells: From Genes to Therapy*, C. Peschle, Editor, *Annals of the New York Academy of Sciences* 511:447–458 (1987).

In addition to the cancer immunotherapies, adoptive immunotherapy has applications for deficiency or dysfunction of T cells associated with several diseases and conditions. Viral infections that respond to IFN-alpha include recurrent herpesvirus (HSV, VZV, CMV), hepatitis B virus, and papillomavirus. Spiegel, R. J., "The alpha interferons: Clinical overview." *Seminars in Oncology* 14:1 (1987). The patients suffering from these viral infections may have their lymphocytes processed using an autolymphocyte therapy that stimulates the production of cytokines.

ALT is also being evaluated in the treatment of patients infected with HIV. Various immune system defects and abnormalities are associated with AIDS and HIV infection, most notably, there is a functional deficiency in CD4+T cells. However, induction of T cell mediated responses could contribute to the accelerated destruction of the host immune system, since activation of T cells is required for HIV entry into CD4+ cells. Although the immune mechanism is still being evaluated, some reports indicate that CD8+ T cells can play an important role in the control of HIV production. O. Martinez-Maza, "HIV-Induced Immune Dysfunction and AIDS-Associated Neoplasms," in *Biological Approaches to Cancer Treatment: Biomodulation*, M. Mitchell, Editor, McGraw-Hill, Inc., Chapter 9, pages 181–204 (1993).

Periodontal diseases may also be treated with adoptive immunotherapy. Although gingivitis and periodontitis are caused by dental bacterial plaque, there is a reluctance to treat this disease with antibiotics because of the problems with antibiotic-resistant strains. Lymphocytes from individuals with periodontal disease may be treated in vitro with general immune enhancing mitogens or with dental plaque antigens to mediate an immune response. Engel et al., "Mitogen-induced hyperproliferation response of peripheral blood mononuclear cells from patients with severe generalized periodontitis: Lack of correlation with proportions of T cells and T cell subsets," *Clinical Immunology and Immunopathology* 30:374 (1984).

Additionally, adoptive immunotherapy may be used to generally boost the immune system by improving an immune cell mediated response. With age, the functions of the immune system show some evidence of decline. For instance, the DTH response, an immune cell mediated event, has been documented to be reduced with age. Miller, "Age-associated decline in precursor frequency for different cell-mediated reactions with preservation of helper and cytotoxic effect per precursor cell," *Journal of Immunology* 132:63 (1984) and Saltzman and Peterson, "Immunodeficiency of the elderly," *Review of Infectious Diseases* 9:127 (1987).

One of the major challenges associated with adoptive immunotherapy is the identification of in vitro assays that are useful in predicting in vivo efficacy. Most notable in this regard is with LAK therapies in the lack of correlation between the cytotoxic function of LAK cells and the in vivo outcome. As reported in *Biological Approaches to Cancer Treatment: Biomodulation* (Mitchell, Ed., McGraw-Hill, Inc. (1993)), the results of LAK and IL-2 therapies give conflicting conclusions: In a protocol for treating patients with processed LAK cells and a low dose of IL-2, with one study there was a significant patient response rate and reduced toxicity. Yet, a similar trial resulted in greater patient toxicity and fewer responses (Rubin and Lotze, "Adoptive Cellular Immunotherapy of Cancer," Chapter 16, pages 379–409, supra.)

Since adoptive immunotherapy is based primarily on the infusion of in vitro processed immune cells into the patient, it is a goal of researchers to develop an accurate measurement of in vitro activity of the processed immune cells which can be correlated with in vivo efficacy. Development of this assay is hampered by activation mechanisms in lymphocytes. T lymphocytes, for example, require at least two different signals, generated by two different cell surface-binding events, for full activation. Proliferation, in response to antigen recognition, is mediated primarily by all autocrine growth pathway, in which the responding T cell secretes its own growth-promoting cytokines and also expresses cell surface receptors for these cytokines. The first signal is the binding of the T cell receptor (TCR):CD3 complex to antigen processed and presented in association with MHC class II antigen on the surface of antigen presenting cells (APCs). The second signal may be triggered by activated APCs either as secreted cytokines produced by the APCs binding to specific receptors on T cells or by cell-cell interaction through accessory membrane bound molecules.

These two signals can be replicated in vitro by the combination of protein kinase C (PKC) activators, such as phorbol esters, and calcium ionophores, such as ionomycin, which increase cytoplasmic calcium concentrations. Neither PKC activators nor calcium ionophores are sufficient alone for full T cell activation.

A number of other mitogens have been used with in vitro cultures to activate and assess human lymphocyte function. Some lectins, such as phytohemagglutinin (PHA) and concanavalin A (Con A), activate T lymphocytes. Other lectins, such as pokeweed mitogen (PWM) activate B lymphoctyes. These mitogens act in a cell-cell dependent manner or require antigen presenting cells (APCs) to activate the lymphoctyes. The degree of lymphocyte activation in vitro is also a function of the cellular regulatory influences present in the culture. Suppressor or helper T, B, and mononuclear cells are all capable of modifying the final degree of proliferation in the specifically stimulated cell population. Some mitogens, particularly Con A, are known to activate suppressor T cells, which may markedly reduce the proliferative response in these cultures. Due to the variability in the nonspecific stimulation of lymphocytes with these mitogens, their use as stimulants for lymphocyte activation in in vitro assays for adoptive cell immunotherapy is unsatisfactory. Since adoptive immunotherapy is based principally on the infusion of modified or activated immune cells into the patient, an accurate in vitro assay measuring the degree of activation of the processed immune cell would be an important first step in correlating in vitro response with in vivo efficacy.

SUMMARY OF THE INVENTION

The inventors have discovered that a single stimulant, which acts intracellularly as a probe to detect the presence of previous activation in non-resting immune cells, will stimulate these immune cells to activity. The stimulants of this invention are therefore chosen for their ability to act intracellularly by effectively stimulating non-resting immune cells to activity at the dose used for stimulation. Yet, the stimulant will not effectively stimulate, by having no activation or by having a significantly lower level of activation of, resting immune cells. The assay of this invention is distinct from those assays that measure the activity of immune cells following stimulation with stimulant(s) that activate resting immune cells, and therefore, do not readily distinguish between resting and non-resting immune cells.

The inventors have discovered that a stimulant, which acts directly as a probe to detect the presence of previous activation in non-resting immune cells, will stimulate or induce the nonresting immune cells to activity. This stimulant, however, will not effectively stimulate to activity resting immune cells, which have not had previous activation. This invention is thus directed to a method for measuring the degree of activation of immune cells by stimulating immune cells to activity with a stimulant and then measuring the activity of the immune cells. Degree of activation refers to all indication of the quantitative response of non-resting immune cells (NR) compared with that of resting immune cells (R). This may be measured as the ratio (NR/R) or difference (NR-R) of the response of non-resting cells compared to the response of resting cells. Appropriate stimulants at concentrations useful in the practice of this invention are discriminatory, meaning that they will effectively stimulate non-resting immune cells to activity, but will not effectively stimulate resting immune cells to activity. The stimulants of the invention act directly on target cells, meaning that the stimulants exert effects on or in the target cells, without requiring accessory cells or cell-cell interactions.

In the assay of this invention, the stimulant will stimulate to activity those immune cells that have had previous activation, that is, non-resting immune cells. The activity of these stimulated immune cells can then be measured. In most cases, the activity of the stimulated non-resting cells is compared by ratio or difference to a control value, typically the activity of a sample of stimulated resting immune cells. In one embodiment, the resting cells are nonactivated peripheral blood mononuclear cells. Following measurement of the activity of a sample of these cells, the remaining cells are then activated by any of a variety or conventional methods familiar to those skilled in the art, such as stimulation by antigen, PHA, cytokines, antibody, allogeneic cells, or other foreign cells. The activated cells are next stimulated and their activity measured. The increase in stimulant-induced activity attributable to activation can be expressed as the ratio or the difference between the activities of the non-resting and resting cells. In another embodiment, the proportion of non-resting cells relative to resting cells is measured in a test immune cell sample. This determination may be made on immune cell populations which have different degrees of heterogeneity with respect to their relative numbers of resting and non-resting cells. In such an assay, the cells are stimulated to activity with a discriminatory stimulant. The measured activity is compared to a control value, such as the activity of a control sample of known resting or known non-resting cells, to assess the proportion of resting to non-resting cells in the test sample.

One of the primary uses of this assay is to correlate the degree of activity of non-resting immune cells as stimulated by the stimulant with in vivo potency in a clinical outcome for a particular therapy. By assaying the degree of activation of a sample of activated immune cells prior to infusion of the cells into a patient, it is possible to predict the clinical outcome of ex vivo therapy using the primed immune cells. With sufficient testing and evaluation, a standard can be ascertained which represents the minimum activity levels of stimulated, primed immune cells which correlates with an acceptably favorable clinical outcome. In this way, the activation level of a particular sample of ex vivo activated cells could be compared to the previously determined standard value representing clinical efficacy; based on the comparison, appropriate decisions could be made as to whether or not to infuse the cells into the patient or whether to further process the cells.

For those assayed immune cells that do not meet the established standard for minimum activity levels, the cells may be retreated or stimulated according to the protocol for that therapy to activate the cells. Alternatively, the cells may be replaced and the replacement cells then treated or primed according to protocol. The results from the assay may also be utilized to monitor the protocol for activating the cells, for example, evaluating the type and amount of stimulants used to prime the cells and the length of time the cells are activated prior to infusion into patients. The assay may also be used to regulate the infusion of the immune cells by defining or modifying, or both, the treatment by the number of activated cells infused.

BRIEF DESCRIPTION OF THE DRAWINGS

FIGS. 1A–1C are graphs showing proliferation of the putatively non-resting immune cells, termed ex vivo activated (EVA) cells, stimulated with phorbol myristate acetate (PMA). Apheresis-derived peripheral blood mononuclear cells (PBMC), which are resting cells, and the resulting EVA cells from 3 different patients, prepared or activated as detailed in the Examples, were cultured at $1\times10^6$ cells/ml in 96-well tissue culture plates for 48 hours at 37° C. with varying concentrations of PMA and were labelled with $^3$H-TdR for the last 6 hours of culture. Each of the FIGS. 1 A, 1B and 1C represents the results obtained with cells from one patient. ○, apheresis-derived PBMC; ●, EVA cells.

FIGS. 2A and 2B are bar graphs showing the proliferation of CD4+ and CD8+ EVA cells in response to PMA. EVA cells were depleted of CD4+ and/or CD8+ cells by treatment with mAB and magnetic particle immunoadsorption as detailed in the Examples. The negatively-selected cells were adjusted to an equal concentration of cells ($1\times10^6$/ml) as the untreated cells and both populations stimulated for proliferation with 1 ng/ml PMA. In FIG. 2A, the EVA cell samples were depleted of both CD4+ and CD8+ cells. In FIG. 2B, the EVA cell samples were depleted of either CD4+ or CD8+ cells.

FIG. 4A shows the percentage of CD25(IL-2R) positive cells and FIG. 4B shows the percentage of CD45RO positive cells from each of these EVA cell samples plotted against the amount of 3H-TdR incorporated for that sample.

FIGS. 5–7 are graphs showing cytokine production by EVA cells stimulated with PMA. Apheresis.-derived PBMC and the resulting EVA cells from 3 different patients were cultured at $1\times10^6$ cells/ml in 48-well tissue culture plates for 48 hours at 37° C. with varying concentrations of PMA. The cell free supernatants were then collected and stored at −70° C. The supernatants were subsequently ELISA assayed for gINF as shown in FIGS. 5A, 5B and 5C; GM-CSF as shown in FIGS. 6A, 6B and 6C: and TNF-alpha as shown in FIGS. 7A, 7B and 7C. Each figure represents the results obtained with EVA cells from one patient. ○, apheresis-derived PBMC; ●, EVA cells.

DETAILED DESCRIPTION OF THE INVENTION

Figure 2B:
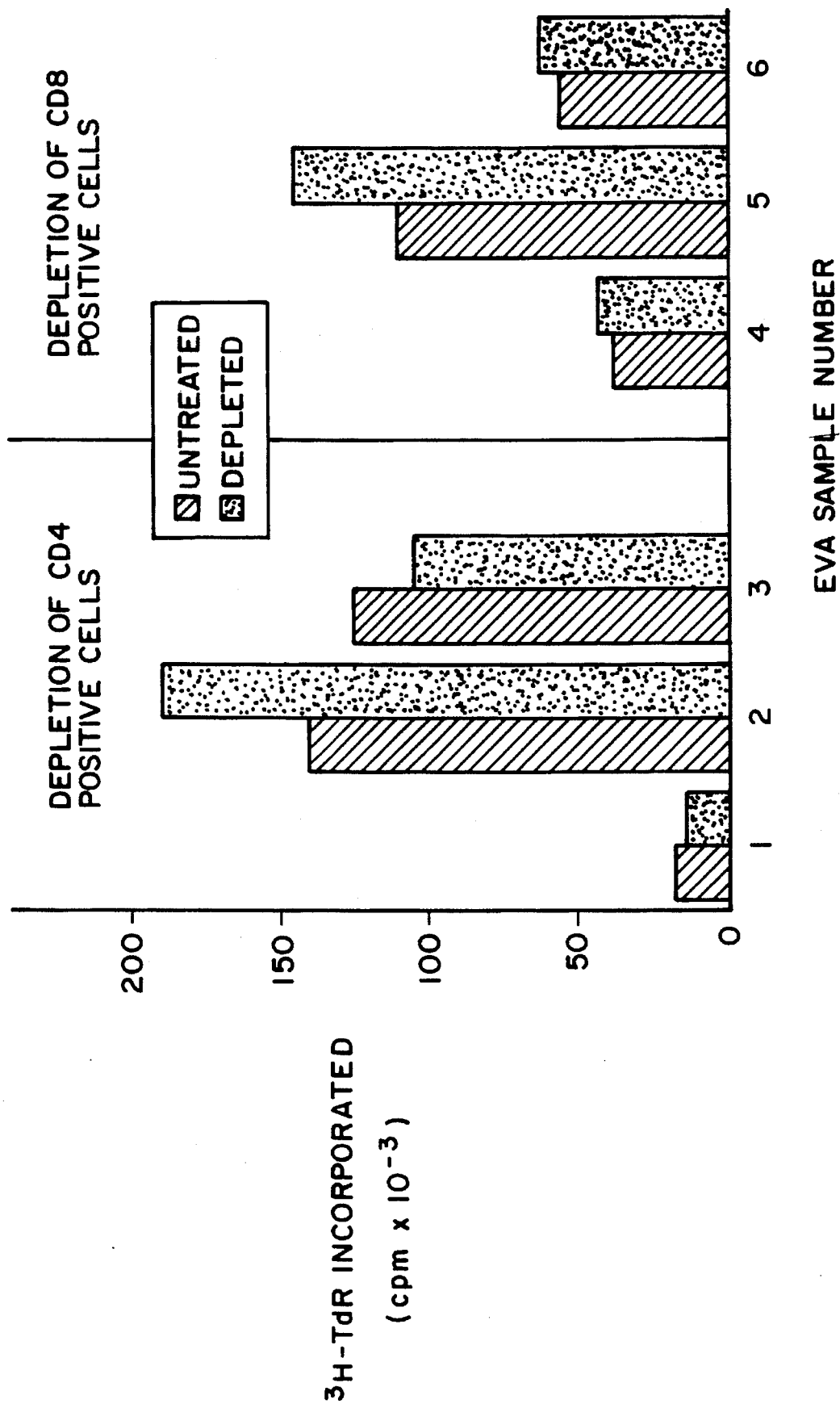

The stimulants of this invention act directly as activation probes and are able to elicit evidence of a primed state, or stage of immune cell activation. In the selection of stimulants for use in this invention, the stimulants which can be used are direct acting, meaning that they act independently from contributions of accessory cells and are independent from contributions of antigens or antigen presenting cells.

The stimulants of this invention are drugs, chemicals, compounds, agents, hormones, or other signals which are chosen for their ability to effectively induce non-resting immune cells to activity at the dose used for stimulation. Yet, the stimulant will not effectively induce resting immune cells to activity. These stimulants are therefore discriminatory between non-resting and resting target cells, meaning that at appropriate dosage levels or at appropriate combinations of sub-threshold stimulants, the compounds are capable of inducing activity in non-resting but not in resting immune cells. This assay is distinct from prior art assays that utilize stimulant(s) which activate resting immune cells, and therefore, do not distinguish or discriminate between resting and non-resting immune cells.

"Immune cells" as used herein, include both non-resting and resting cells, and is meant to include any cells of the immune system that may be assayed, including, but not limited to, B lymphocytes, also called B cells, T lymphocytes, also called T cells, natural killer (NK) cells, lymphokine-activated killer (LAK) cells, monocytes, macrophages, neutrophils, granulocytes, mast cells, platelets, Langerhans cells, stem cells, dendritic cells, peripheral blood mononuclear cells, tumor-infiltrating (TIL) cells, gene modified immune cells including hybridomas, drug modified immune cells, and derivatives, precursors or progenitors of the above cell types.

"Non-resting immune cells" are immune cells that have previously been primed, sensitized, activated, or changed biochemically, such that they gain and maintain the ability to be stimulated to activity by a discriminatory stimulant. Such sensitization may occur through exposure to an activating or inducing signal or signals, in any way, either by in vivo, by in vitro, or by ex vivo means. Non-resting immune cells have therefore been "primed" to respond to further stimulation by a discriminatory stimulant, meaning a dose of a stimulant which effectively induces non-resting but not resting immune cells to activity. A primed immune cell has stable biochemical changes induced by prior activation, such that the cell is able to become fully activated with less than a full complement of activation signals. A primed immune cell is able to maintain itself in a particular phase of its cell cycle, enabling it to respond to a stimulant which consists of less than a full complement of activation signals. In vivo activation may be by natural immune response to an antigen, mitogen, or cytokine. In addition, in vivo activation can be by introducing antigens into a human or nonhuman patient, or by immunotherapy, for example with alpha- or gamma-interferon, with IL-2, or with infusion of primed cells in autolymphocyte therapy (ALT). In vitro activation may be by processing immune cells with antibodies, mitogens, tumor cells, cell targets, lymphokines, antigens, or subunit pieces thereof, as is known in the art. Ex vivo activation is also by processing immune cells with antibodies, mitogens, tumor cells, cell targets, lymphokines, antigens, or subunit pieces thereof, as is typically done for adoptive immunotherapy for reinfusion into the patient.

"Resting immune cells" are those immune cells that have not previously been adequately primed; they are incapable of being induced to activity by a discriminatory stimulant.

The assays of the invention measure the degree of activation of sample immune cells. Sample immune cells refer to immune cells contained in samples from any source, including from a human patient, human donor, animal, or tissue cultured cell line. The immune cell sample can be derived from peripheral blood, lymph nodes, bone marrow, thymus, any other tissue source including in situ or excised tumor, or from tissue or organ cultures. The sample may be fractionated or purified to generate or enrich a particular immune cell subset before analysis. In different embodiments of the assay procedure, the sample may be obtained before, during, or after in vitro or ex vivo culture. The immune cells can be separated and isolated from their source by standard techniques and then primed by culturing the immune cells according to the protocol for the desired treatment. The immune cells will most typically be autologous, although allogeneic or syngeneic immune cells may also be used. If allogeneic cells are used for immunotherapy, then the cells should be matched for HLA and MHC compatibility with the host patient's cells prior to infusion. For some immunotherapies, typically with animal testing, the immune cells may be xenogeneic.

The method of the invention may also be applied to measuring the degree of activation of non-immune cells, such as fibroblasts, neoplastic cells. hepatocytes, or cells altered by gene therapy or infection with bacteria, virus, fungi, or parasites. In these cells, activation may be measured by assessing any cell function which responds to the stimulant, including such functions as cell proliferation, production of protein or other cell product, viral production, or cell differentiation. In one embodiment, the activity of hepatocytes is measured by their uptake of radiolabeled amino acids. The activity of normal control ("resting") hepatocytes is compared with that of virus-infected ("non-resting") hepatocytes.

"Activity" or "activation" is the ability of immune cells to respond and exhibit, on a measurable level, an immune function. Measuring the degree of activation refers to a quantitative assessment of the capacity of immune cells to express enhanced activity when further stimulated as a result of prior activation. The enhanced capacity may result from biochemical changes occurring during the activation process that allow the immune cells to be stimulated to activity in response to low doses of stimulants. By revealing the results of such changes, this assay may be used to predict the therapeutic benefits of these cells.

The stimulant to be used in the methods of the invention is used at a concentration which stimulates non-resting but not resting cells. Where more than one co-stimulant are used in the methods of the invention, the co-stimulants are used in too low a dose, or in too incomplete all array, to stimulate resting cells. Such a concentration may be readily established for any given stimulant and for ally target cell type of interest as follows. Samples of known non-resting cells of the target cell type, and samples of known resting target cells, are treated with a range of concentrations of the stimulant. The activity of the cells is monitored by measuring all appropriate cellular activity, as described above. All appropriate concentration range of stimulant is one which optimally differentiates between non-resting and resting states.

One class of stimulants that may be used in this invention includes protein kinase C activators. Protein kinase C activators directly or indirectly induce the enzyme protein kinase C to become activated and catalyse a cascade of biochemical changes both in and on the surface of a cell. In the presence of an appropriate complement of immune cell activators or co-stimulants, these changes result in full activation of the cell with consequent enhancement of cellular function or activity. Protein kinase C activators include phorbol esters, such as phorbol myristate acetate (PMA) and phorbol dibutyrate, as well as 1,2-dioctanoylglycerol. Many phorbol esters are also tumor promoters, which are compounds able to promote neoplasia, or loss of controls on normal cell growth, in target cells. Stimulants for use in the invention therefore also include tumor promoters, such as teleocidin and 3-methyl-cholanthrene. PMA mimics a natural intracellular compound, diacylglycerol (DAG), so that DAG and DAG analogs may also be used as stimulants. Calcium ionophores may also be used, such as ionomycin and calcimycin. Analogs of these compounds may also be used as a stimulant in the assays. In some cases, a combination of stimulants may be useful in the methods of the invention, as long as the dosages are chosen to selectively stimulate non-resting but not resting cells.

Once the stimulant is chosen, it is routine skill in the art to test and evaluate the appropriate dose requirement for the cells to determine the degree of activation of non-resting immune cells and resting immune cells. Moreover, the amount of the stimulant will vary depending on the number or weight basis of the immune cells being stimulated.

In this invention, the inventors found that low doses of PMA only, without a secondary signal, in the dose range from about 1 ng/ml to about 10 ng/ml, stimulated primed immune cells to activity by proliferation and production of cytokines. At PMA dose levels of 0.1 ng/ml, the immune cells did not substantially proliferate. With these same dose ranges, the resting immune cells were not effectively stimulated to activity.

Using ionomycin without complementary co-stimulants, the inventors found that a dose 50 ng/ml of ionomycin promoted an enhanced proliferative response of primed lymphocytes cells. Using this same dosage amount with resting lymphocyte cells, the immune cells did not substantially proliferate when stimulated with the ionomycin. A combination of ionomycin and one or more co-stimulants, such as PMA, may be used in concentrations to yield a discriminatory response.

The immune cells may be cultured with the stimulant at cell concentrations of approximately $1 \times 10^6$ lymphocytes per milliliter. The stimulant is added on a weight basis, but will typically range between 1 ng/ml to about 10 ng/ml and may range up to 50 ng/ml or more. Cultures are incubated for a time sufficient for stimulants have produced their maximal effect on stimulating the immune cells to activity. The typical time will be for about 0.5 to 150 hours.

There are a number of variables that can affect the results of this assay system. These variables include the concentration of the cells, the geometry of the culture vessel, contamination of the cultures, the dose of the stimulant, the incubation time of the cultures, and the techniques of harvesting the cells. All of these variables are within routine experimentation of one of the skill of the art to determine the optimum incubation conditions for the culturing.

If the optimal dose range of the chosen stimulant is not known, the stimulant may be added to the cell culture in varying concentrations on a weight basis, usually over a 2–3 log range. The immune cell function assays, as described below, can then be used to determine the degree of activation of the immune cell as stimulated by the stimulant. In the preferred embodiment, the optimal dosage will be determined by cell proliferation as measured by radiolabeled thymidine incorporation in DNA synthesis, as discussed below.

In the method of this invention, the stimulant will stimulate to activity those immune cells that have had previous activation and have maintained the primed state. The activity of these stimulated immune cells can then be measured. Immune cell activity that may be measured include, but is not limited to, (1) cell proliferation by measuring the cell or DNA replication; (2) enhanced cytokine production, including specific measurements for cytokines, such as gIFN, GM-CSF, or TNF-alpha; (3) cell mediated target killing or lysis; (4) cell differentiation; (5) immunoglobulin production; (6) phenotypic changes; (7) production of chemotactic factors or chemotaxis, meaning the ability to respond to a chemotactin with chemotaxis; (8) immunosuppression, by inhibition of the activity of some other immune cell type; (9) ability to bolster the response of resting immune cells to a simulant, as measured with addback assays; and (10) apoptosis, which refers to fragmentation of activated immune cells under certain circumstances, as an indication of abnormal activation.

Cell Proliferation Assay

Activated immune cell proliferation is intended to include increase in cell number, cell growth, cell division, or cell expansion, as measured by cell number, cell weight, or by incorporation of radiolabelled nucleic acids, amino acids, proteins, or other precursor molecules. As one example, DNA replication is measured by incorporation of radioisotope labels. In the preferred assay, cultures of immune cells stimulated by the stimulant can be measured by DNA synthesis by pulse-labeling the cultures with tritiated thymidine ($^3$H-Tdr), a nucleoside precursor that is incorporated into newly synthesized DNA. Thymidine incorporation provides a quantitative measure of the rate of DNA synthesis, which is usually directly proportional to the rate of cell division. The amount of $^3$H-labeled thymidine incorporated into the replicating DNA of cultured cells is determined by scintillation counting in a liquid scintillation spectrophotometer. Scintillation counting yields data in counts per minute (cpm) which may then be used as a standard measure of immune cell responsiveness. The cpm in resting immune cell cultures may be either subtracted from or divided into cpm of the primed immune cells, which will yield a stimulation index ratio.

Flow cytometry can also be used to measure proliferation by measuring DNA with light scatter, Coulter volume and fluorescence, all of which are techniques that are well known in the art.

Enhanced Cytokine Production Assay

Another response indicator that may be employed after activation and stimulation is the ability of the cells to secrete cytokines, lymphokines, or other growth factors. Cytokine production, including specific measurements for cytokines, such as gIFN, GM-CSF, or TNF-alpha, may be made by radioimmunoassay (RIA), enzyme-linked immunoabsorbent assay (ELISA), bioassay, or measurement of messenger RNA levels. In general, with these immunoassays, a monoclonal antibody to the cytokine to be measured is used to specifically bind to and thus identify the cytokine. Immunoassays are well known in the art and can include both competitive assays and immunometric assays, such as forward sandwich immunoassays, reverse sandwich immunoassays and simultaneous immunoassays.

In each of the above assays, the sample-containing cytokine is incubated with the cytokine-specific monoclonal antibody under conditions and for a period of time sufficient to allow the cytokines to bind to the monoclonal antibodies. In general, it is desirable to provide incubation conditions sufficient to bind as much cytokine and antibody as possible, since this will maximize the signal. Of course, the specific concentrations of antibodies, the temperature and time of incubation, as well as other such assay conditions, can be varied, depending upon various factors including the concentration of cytokine in the sample, the nature of the sample, and the like. Those skilled in the art will be able to determine operative and optimal assay conditions for each determination by employing routine experimentation.

Cell-Mediated Target Cell Lysis Assay

Another type of indicator for degree of activation is immune cell-mediated target cell lysis, which is meant to encompass any type of cell killing, including cytotoxic T lymphocyte activity, apoptosis, and the induction of target lysis by molecules secreted from non-resting immune cells stimulated to activity. Cell-mediated lympholysis techniques typically measure the ability of the stimulated immune cells to lyse $^{51}$Cr-labeled target cells. Cytotoxicity is measured as a percentage of $^{51}$Cr released in specific target cells compared to percentage of $^{51}$Cr released from control target cells. Cell killing may also be measured by counting the number of target cells, or by quantifying an inhibition of target cell growth.

Cell Differentiation Assay

Cell differentiation may be assessed in several different ways. One such method is by measuring cell phenotypes. The phenotypes of immune cells and any phenotypic changes can be evaluated by flow cytometry after immunofluorescent staining using monoclonal antibodies that will bind membrane proteins characteristic of various immune cell types.

A second means of assessing cell differentiation is by measuring cell function. This may be done biochemically, by measuring the expression of enzymes, mRNA's, genes, proteins, or other metabolites within the cell, or secreted from the cell. Bioassays may also be used to measure functional cell differentiation.

Immune cells express a variety of cell surface molecules which can be detected with either monoclonal antibodies or polyclonal antisera. Immune cells that have undergone differentiation or activation can also be enumerated by staining for the presence of characteristic cell surface proteins by direct immunofluorescence in fixed smears of cultured cells.

Mature B cells can be measured in immunoassays, for example, by cell surface antigens including CD19 and CD20 with monoclonal antibodies labeled with fluorochromes or enzymes may be used to these antigens. B cells that have differentiated into plasma cells can be enumerated by staining for intracellular immunoglobulins by direct immunofluorescence in fixed smears of cultured cells.

Immunoglobulin Production Assay

B cell activation results in small, but detectable, quantities of polyclonal immunoglobulins. Following several days of culture, these immunoglobulins may be measured by radioimmunoassay or by enzyme-linked immunosorbent assay (ELISA) methods.

B cells that produce immunoglobulins can also be quantified by the reversed hemolytic plaque assay. In this assay, erythrocytes are coated with goat or rabbit anti-human immunoglobulins. These immunoglobulins are mixed with the activated immunoglobulin-producing lymphocytes and semisolid agar, and complement is added. The presence of hemolytic plaques indicates that there are immunoglobulin-producing cells.

Chemotactic Factor Assay

Chemotactic factors are molecules which induce or inhibit immune cell migration into or out of blood vessels, tissues or organs, including cell migration factors. The chemotactic factors of immune cells can be assayed by flow cytometry using labeled monoclonal antibodies to the chemotactic factor or factors being assayed. Chemotactic factors may also be assayed by ELISA or other immunoassays, bioassays, messenger RNA levels, and by direct measurements, such as cell counting, of immune cell movements in specialized migration chambers.

Addback Assays

When added to fresh peripheral blood mononuclear cells, autologous ex vivo activated cells exhibit an enhanced response to a "recall" antigen, which is an antigen to which the peripheral blood mononuclear cells had previously been exposed. Primed immune cells stimulated with the stimulant should enhance other immune cells response to a "recall" antigen when cultured together. These assays are termed "helper" or "addback" assays. In this assay, primed immune cells, either with or without the stimulant, are added to untreated, usually autologous immune cells to determine the response of the untreated cells. A variation of this assay is to add the stimulated immune cells, either with or without the stimulant, and measure the helper function of tire immune cells ready for infusion. The added primed cells may be irradiated to prevent their proliferation, simplifying the measurement of the activity of the untreated cells. These assays may be particularly useful in evaluating cells for blood exposed to virus. The addback assays can measure proliferation, cytokine production, and target cell lysis as described above.

Apoptosis

Apoptosis is another immune cell activity which may be assessed to measure the degree of immune cell activation. Apoptosis is a type of programmed cell death, exhibited by an atypicalty activated cell in response to further stimulation. The assay of the invention is useful for assessing the tendency of ex vivo activated cells to undergo apoptosis either in vitro or in vivo. The ex vivo activated cells are stimulated with the discriminatory stimulants of the invention, and apoptosis is measured. An enhanced apoptosis rate may be correlated with poor clinical efficacy after the cells are reinfused into a patient.

Uses of In Vitro Assays Measuring the Degree of Activation of Immune Cells Stimulated to Activity The assay of the invention may be utilized for many different purposes. The effectiveness of a protocol in producing activated cells may be evaluated with the methods of the invention, and the activation protocol may be adjusted to maximize the production of cells which show optimal immune activity of the type desired. In one aspect of such an evaluation, reagent and cell stability may be assessed by measuring product cell activation after varying such factors as time, temperature and other characterisitcs of reagent or cell storage.

In another aspect of use of the invention, the assay may be useful in characterising the identity, purity and potency of therapeutic cell products to comply with FDA and other regulatory agency regulations.

The assay may be used to predict the therapeutic benefits of infusing non-resting cells into a patient. Using the assay to assess the degree of activation of the non-resting cells, clinical outcome of a patient infused with the cells may be predicted based on the degree of activation of the stimulated immune cells. Clinical outcome may be assessed by such measures as length of patient survival, quality of life measurements, changes in any indicators of medical function such as clinical chemistries, size of tumors, changes in load of virus, bacteria, fungus, or parasite, toxicity of the therapy, or delay in time of recurrence of the disease, or other assessments.

The assay may also be used to provide a standard for predicting clinical outcome of patients based on degree of activation of stimulated immune cells prior to infusion of the stimulated immune cells into the patients for adoptive immunotherapy. In this use, immune cells are obtained from different patients. Cultures of the immune cells, with each culture containing immune cells from one patient, are stimulated to activity with a direct-acting discriminatory stimulant to produce cultures of stimulated immune cells. The degree of activation of each culture of stimulated immune cells is next measured, and a portion of each culture of stimulated immune cells is infused into the patient from whom the immune cells were obtained. The clinical outcome of each patient is evaluated as an indication of in vivo efficacy of treatment with the infused stimulated cells. Based on the results of a group of treated patients, a standard minimum degree of activation is established which correlates with in vivo efficacy. After this standard is established, the degree of activation of a subsequent patient's primed immune cells can be compared to the standard value, and appropriate treatment decisions can be made based on whether or not the patient's cells are primed to the degree previously found to correlate with clinical efficacy.

Information on degree of cell activation of a patient's immune cell sample may be useful for quality control purposes, since an insufficiently activated sample may be reactivated. In other cases, ex vivo treated cells of a given patient may not show enough activation to corellate with clinical efficacy and justify infusion of the cells; that patient might be evaluated for treatment with other methods, or the reduced activation level of his cells might be offset by infusing him with increased numbers of cells. In yet another case, the degree of activation of cells from different patients might be monitored by assaying the cells after different time periods or other protocol changes in the ex vivo activation protocol. For each patient, the protocol may be customized to produce optimally activated cells, for example by culturing the cells for the time period which results in highest assayed activation for each cell sample.

The assays may also be useful for evaluating the immune cell status of a patient, meaning the state of activation of peripheral blood mononuclear cells taken from a patient and assayed without further treatment. Abnormally elevated levels of activated lymphocytes in a patient may indicate infection, cancer, or other states of immune stimulation. In some cases, the assay might prove valuable for confirming adequate response to a vaccination. The immune cell status of a patient is evaluated by obtaining a sample of immune cells from the patient, and stimulating the immune cells to activity with a discriminatory stimulant. The activity of the immune cells following stimulation is measured, and compared to a control value. The control value is an activity measurement representative of a particular degree of immune cell activation, either that of the patient's immune cells at another time, or that of other immune cells. For example, the degree of activation of a patient's cells may be followed over time, with samples measured for degree of activation at successive times, in which case the control value might be that of the first sampling of immune cells. In other cases, an appropriate control value might be one which represents the state of activation of immune cells with a known degree of immune cell activation. To obtain these cells, blood might be obtained from groups of either healthy people without stimulated immune systems, or from people with immune systems known to be highly stimulated.

These assays are useful in adoptive immunotherapy which processes immune cells to treat cancers, infectious diseases, autoimmune diseases, or immune deficiency diseases.

The assays of this invention may be configured into a kit. The kit may include two or more container means for separately storing primed immune cells and resting immune cells prior to testing. The kit may contain containers for in vitro culturing of the stimulant and the immune cells, typically these culturing means are flat-bottom plates. The kit may then have a plurality of containers holding reagents to be used in the culturing of the cells with the stimulant, such as the stimulant and culture nutrients. The kit may also have a plurality of containers for the chosen assay, such as enzymes, radiolabels, antibodies, and the like. In addition, the kit may include a plurality of containers each of which comprises different, predetermined and known amounts of lymphocytes, or other cells, for use as a control. These latter containers can then be used to prepare a standard curve from which can be interpolated the results obtained from the sample immune cells containing the unknown amount of activity.

The following examples further describe the materials and methods used in carrying out the invention. The examples are not intended to limit the invention in any manner.

EXAMPLES

Introduction

Autolymphocyte therapy (ALT) is an outpatient form of adoptive immunotherapy based on the infusion of approximately $10^9$ autologous, activated peripheral blood mononuclear cells (PBMC). Patients also receive oral cimetidine to block suppressor T cell activity. ALT has been shown to be effective in the treatment of metastatic renal cell carcinoma as indicated by significant survival prolongation and the induction of durable tumor responses, and is accompanied by only minimal toxicity. The ex vivo activated (EVA) cells used in ALT are generated by a unique 2-stage process in which patient apheresis PBMCs are first stimulated with 25 ng/ml OKT3 for 72 hours to produce a cytokine-enriched culture supernatant, T3CS, which is utilized in stage 2 to generate the EVA cells used therapeutically. T3CS is a heterogeneous mixture of monokines and lymphokines including IL1-alpha, IL1-beta, IL6, TNF-alpha, TNF-beta, gIFN, and GM-CSF, together with OKT3 at approximately 10–20 ng/ml. Growth factors such as IL2, IL3, IL4 and IL7 were not detectable in T3CS samples. The EVA cells utilized in ALT were generated by a 5-day culture of patient apheresis PBMCs with autologous T3CS. An extensive phenotypic analysis revealed that EVA cells were 87% CD3+ T cells comprised of 65% CD4+ cells and 26% CD8+ cells. Greater than 70% of EVA cells were CD45RO+ memory cells including 33% CD4+ memory cells and 25% CD8+ memory cells. All of these proportions were significantly increased relative to the PBMCs from which the EVA cells were derived. EVA cells had very high levels of activated cells—37% were CD25+ (IL2R+) and 41% were MHC class II-positive T cells, increased from 2% and 7%, respectively, in PBMCs. The ability of EVA cells to proliferate and produce cytokines in vitro was determined by measuring the responses to EVA cells to a low doses (1 ng/ml) of phorbol myristate acetate (PMA)—a protein kinase C activator. EVA cells, relative to the PBMCs from which they were derived, were clearly primed to respond to this dose of PMA, exhibiting substantial proliferation and gIFN, GM-CSF and TNF-alpha production. Depletion experiments revealed that EVA cells responding to PMA were almost exclusively T cells including both CD4+ and CD8+ cells. In addition, CD45RO+ memory and CD45RA+ naive cells proliferated in response to PMA as did both IL2R+ and IL2R cells. EVA cells did not proliferate or produce cytokines spontaneously when cultured in medium alone, nor did unactivated PBMCs stimulated with PMA. The calcium ionophore, ionomycin, was also evaluated as a stimulant for EVA cells. When used alone, ionomycin was effective in stimulating EVA cells to proliferate and a comparison was made between EVA cells and PBMCs from which they were derived.

In the statistical analysis in the examples that follow, the values for p were calculated by use of the two-tailed Student's t test assuming unequal variances.

1. Isolation of apheresis-derived PBMCs

Patients diagnosed with mRCC were apheresed utilizing a standard Haemonetics (Haemonetics Corporation, Braintree, Mass.) V-50 Apheresis System machine. The apheresis cell product (ACP), approximately $2\times10^9$ cells, was collected into 600 ml Baxter Transfer Packs containing acid-citrate-dextrose anticoagulant (Baxter-Fenwal, Deerfield, Ill.) at a 12:1 v/v ratio of ACP to anticoagulant and stored overnight at room temperature prior to processing.

The apheresis cell product was centrifuged at 150 g's in a Beckman GPR centrifuge (Beckman Instruments, Palo Alto, Calif.) for 10 minutes at 22° C. to remove platelets and the cells resuspended in saline (Baxter Healthcare, Deerfield, Ill.). PBMC were then isolated by Ficoll (Lymphoprep, Nycomed Pharma, AS, Oslo, Norway) density gradient centrifugation at 350 g's for 35 minutes at 22° C. using a Ficoll-Hypaque separation bag system (Ethox Corp., Buffalo, N.Y.). The cells collected from the gradient interface were then washed twice with saline and resuspended in tissue culture medium for either conditioned medium production or EVA cell generation as detailed below. Cell numbers and viability were determined with an automated cell counter (Model ZM, Coulter Corp., Hialeah, Fla.) and by trypan blue exclusion, respectively.

2. Preparation of OKT3-induced Conditioned Medium

Apheresis-derived PBMC were cultured at $1\times10^6$ cells/ml in HB104 medium (Irvine Scientific, Santa Ana, Calif.) containing 1% HB104 supplement, 1 mM sodium pyruvate (Whittaker Bioproducts, Walkersville, Md.) and 2 mM L-glutamine (Gibco-BRL, Grand Island, N.Y.). The cells were stimulated with 25 ng/ml OKT3 (Orthoclone OKT3; Ortho Pharmaceutical Corporation, Raritan, N.J.) for 3 days at 39° C. in a humidified 5% $CO_2$ incubator, and the culture supernatant obtained following removal of the cells by centrifugation at 1100 g's for 20 minutes at 22° C. The culture supernatant was then aliquoted into 6–8 samples, stored at −20° C. for 18 to 72 hours and then stored at −70° C. prior to use in generating EVA cells.

3. Generation of EVA Cells

The medium used for culturing PBMCs to generate EVA cells was AIM V medium (Gibco-BRL, Grand Island, N.Y.) containing 0.5% HB104 supplement (Irvine Scientific), 1 mM sodium pyruvate (Whittaker Bioproducts), 50 uM cimetidine (Tagamet, Smith Kline Beecham Pharmaceutical, Cidra, Pa.) and 10 nM indomethacin (Indocin, Merck Sharp & Dohme, West Point, Pa.). The latter two reagents were present to reduce suppressor T cell activity. The apheresis-derived PBMC were cultured at $2\times10^6$ cells/ml and stimulated with 25% (v/v) autologous conditioned medium at 39° C. in a humidified 5% $CO_2$ incubator. After 2 or 3 days culture, one-half of the medium was replaced with AIM V medium containing only sodium pyruvate. Following a total of 5 days culture, the cells were obtained by centrifugation at 1100 g's for 20 minutes at 22° C., washed twice with saline (Baxter Healthcare) and resuspended at $10\times10^6$ cells/ml in "infusion medium" consisting of 1% human serum albumin (HSA; Alpha Therapeutics Corp., Los Angeles, Calif.) and 0.5% dextrose (Abbott Laboratories, Chicago, Ill.) in Lactated Ringers solution (Baxter-Travenol). The EVA cells received 50 rads of gamma radiation to reduce suppressor T cell activity and stored overnight at 4° C. prior to characterization. These procedures were used for generating EVA cells reinfused into patients.

4. Cytokine and OKT3 Composition of T3CS

The OKT3-induced conditioned medium used to generate the EVA cells reinfused into patients receiving ALT was obtained from apheresis-derived PBMC stimulated for 72 hours as detailed above in Section 3.

The cytokine and OKT3 composition of conditioned medium from 15 mRCC patients is shown in Table 1.

Cytokines present in conditioned medium were assayed by ELISA using the following kits: gIFN—Amgen Biologics (Thousand Oaks, Calif.); IL1-beta —Cistron Biotechnology (Pine Brook, N.J.): GM-CSF, IL1-alpha, IL2, IL3, IL4, IL5, IL6, IL7, TNF-alpha, and TNF-beta (Quantikine—Human Immunoassay kits—R&D Systems; Minneapolis, Minn.).

Cytokines produced from EVA cells in response to PMA (as detailed below) were assayed by ELISA using the following kits: gIFN—Endogen, Inc. (Boston, Mass.); GM-CSF and TNF-alpha—R&D Systems.

The amount of OKT3 present in conditioned medium samples was determined by ELISA using the following Vector Laboratories Inc. (Burlingame, Calif.) reagents): horse anti-mouse IgG to capture the OKT3 mouse mAb, biotinylated horse anti-mouse IgG to detect the captured mAb, and a reagent consisting of a complex between avidin and biotinylated horseradish peroxidase to amplify the signal. O-phenylenediamine dihydrochloride (Sigma Chemical Co., St. Louis, Mo.) was used as substrate.

As can be seen in Table I, the majority of samples had significant levels of both monokines and lymphokines including GM-CSF, gINF, IL1-alpha, IL1-beta, IL6, TNF-alpha, and TNF-beta. The levels of gIGN, IL1-beta, IL-6 and TNF-alpha in most of these samples, typically in the 100–1000 pg/ml range, are sufficient to significantly enhance T cell stimulation in vitro. In addition, as shown in Table I, all of the conditioned medium samples tested had low ng/ml levels of OKT3.

TABLE I

Cytokine and OKT3 composition of conditioned medium.

| Patient | GM-CSF (pg/ml) | INFγ (U/ml)* | IL-1α (pg/ml) | IL-1β (pg/ml) | IL-6 (pg/ml) | TNFα (pg/ml) | TNFβ (pg/ml) | OKT3 (ng/ml) |
|---|---|---|---|---|---|---|---|---|
| 1 | 207 | 57 | 285 | 3240 | 352 | 140 | 194 | 15 |
| 2 | 506 | 49 | nd | 575 | 323 | 525 | 719 | 22 |
| 3 | 506 | 55 | 324 | 2889 | 92 | 308 | 569 | 17 |
| 4 | 263 | 37 | — | 257 | 61 | 47 | 381 | 10 |
| 5 | 112 | 8 | 53 | 599 | 23 | 68 | 307 | 18 |
| 6 | 306 | 32 | 290 | 3021 | 379 | 115 | 414 | 45 |
| 7 | 214 | 61 | 445 | 3849 | 1263 | 182 | 163 | 10 |
| 8 | 408 | nd | nd | 262 | 86 | 53 | 182 | 13 |
| 9 | 154 | nd | 11 | 365 | 101 | 83 | 124 | 20 |
| 10 | 184 | 19 | 18 | 1095 | nd | 310 | 782 | 13 |
| 11 | 64 | 15 | nd | 24 | 29 | 35 | nd | 9 |
| 12 | 204 | 10 | 14 | 402 | 61 | 48 | 231 | 12 |
| 13 | 110 | 18 | 43 | 786 | 92 | 77 | 182 | 14 |
| 14 | 242 | 14 | nd | 546 | — | — | 451 | 16 |
| 15 | 420 | 46 | 37 | 1259 | — | — | 526 | 15 |
| MEAN | 260 | 28 | 109 | 1280 | 220 | 153 | 348 | 17 |

Conditioned medium was obtained 72 hours following stimulation of apheresis-derived PBMC with 25 ng ml OKT3.
nd. not detected; —, not determined.
*1 U/ml = 100 pg/ml.

5. Phenotypic Characterization of EVA Cells

EVA cells were generated from apheresis-derived PBMC stimulated with 25% (v/v) autologous conditioned medium were 87±2% CD3+ T cells, consisting of 65±2% CD4+ cells and 26±2% CD8+ cells (Table II). The proportions of all three of these cell types were significantly increased ($p<0.05$) relative to the apheresis-derived PBMC from which the EVA cells were generated. This increase in T cells is almost certainly at the expense of CD14+ cells (monocytes) which decreased from 24% to 3% (Table II). In addition, EVA cells were substantially enriched in activated cells, as CD25 (IL-2R)+ cells increased from 2% to 37%, and MHC class II+ T cells increased from 7% to 41% (Table II). These results are consistent with a polyclonal activation of the T-lymphocytes in these cultures in response to the OKT3 and cytokines present in conditioned medium.

Phenotypes were determined by flow cytometry following immunofluorescent staining using the following mAbs: Coulterclones T3-RD1, T4-RD1, T8-RD1 & -FITC, IL-2R-FITC, 13-FITC, 2H4-RD1 & -FITC, Mo2-RD1, and -FITC (Coulter Corporation, Hialeah, Fla.); and Dako UCHL1-FITC (Dako Corporation, Carpinterai, Calif.). Appropriate labelled isotype-matched mAbs were used as negative controls. Briefly, cells were centrifuged at 1200 rpm (300 g's) for 10 minutes in a Sorvall RT 6000B (Sorvall Instruments, Dupont Company, Wilmington, Del.) and resuspended at $2\times10^6$ cells/ml in AIM V medium with antibiotics (50 ug/ml streptomycin sulfate and 10 ug/ml gentamicin sulfate; Gibco-BRL) containing 1 mM sodium pyruvate (Whittaker Bioproducts) and 2 mM L-glutamine (Gibco-BRL). The cells were incubated at 4° C. for 30 minutes with the amount of mAb recommended by the manufacturer. The cells were then washed with a 5-fold excess of PBS (Dulbecco's, without calcium and magnesium; Whittaker Bioproducts), centrifuged and resuspended at approximately $4\times10^5$ cells/ml in PBS for analysis. The cells were immediately analyzed using a Coulter Epics Profile I or Epics Profile II flow cytometer. All gating was done on viable lymphocytes or, when monocytes were analyzed, on all viable cells.

EVA cells were also characterized for their expression of CD45RA and CD45RO cell surface markers. These markers have been used to define two distinct populations of cells generally regarded as "naive" and "memory" cells, respectively, although the relationship between these cell types is likely to be more complex. On average, the EVA cells were greater than 70% CD45RO+ (Table II), with almost 20% of EVA cell samples having >80% CD45RO+ and CD8+ T cells (33% and 25%, respectively). The proportion of CD45RO+ in these cultures was almost 75% higher (71% compared to 39%, Table II) than in the apheresis-derived PBMC from which they were generated. Interestingly, the proportion of CD45RA+ cells did not change significantly in these cultures. It is likely that at least part of the increase in CD45RO+ cells is due to CD45RA+ cells beginning to express the CD45RO marker. These results demonstrate that EVA cells are predominantly activated T cells consisting of helper/inducer and cytotoxic/suppressor "memory" T lymphocytes.

TABLE II

Phenotypes of mRCC patient apheresis-derived PMBC and EVA cells.

| | % Positive lymphocytes (mean ± SEM) | | |
|---|---|---|---|
| | Apheresis-derived PMBC | EVA cells | Difference |
| CD3+ | 72.0 ± 1.3[†] | 87.0 ± 1.5 | <0.0001 |
| CD4+ | 39.3 ± 1.7 | 64.8 ± 1.9 | <0.0001 |
| CD8+ | 16.7 ± 1.3 | 25.7 ± 2.2 | <0.001 |
| CD25 (IL-2R)+ | 1.6 ± 0.1 | 36.7 ± 3.1 | <0.0001 |
| CD3+ MHC Class II+ | 7.3 ± 0.8 | 40.6 ± 2.8 | <0.0001 |
| CD45RA+ (naive) | 46.0 ± 1.9 | 51.7 ± 2.3 | <0.073 |
| CD45RO+ (memory) | 39.0 ± 1.8 | 70.6 ± 2.1 | <0.0001 |
| CD4+ CD45RO+ | 18.7 ± 1.1 | 33.0 ± 2.4[§] | <0.0001 |
| CD8+ CD45RO+ | 2.8 ± 0.4 | 25.5 ± 2.1[§] | <0.0001 |
| CD14+ | 23.5 ± 1.5[I] | 3.1 ± 0.6[§,I] | <0.0001 |

Apheresis-derived PMBC and EVA (ex-vivo activated) cells were analyzed by flow c for expression of the cell surface markers indicated.
*Values for p were calculated by use of the two-tailed Student's test assuming une variances.
[†]Mean from at least 30 samples except where indicated.
[§]Mean from 15 samples.
[I]% positive mononuclear cells.

6. Cell Depletions

EVA cells (obtained following overnight storage at 4° C. in infusion medium, as detailed above) were depleted of various cell types using magnetic particle separation following treatment with mAb, as detailed below. The antibodies used were T4, T8 from Coulter (Coulter Corp., Hialeah, Fla.). Cells were washed once with AIM V medium with antibiotics (50 ug/ml streptomycin sulfate and 10 ug/ml gentamicin sulfate: Gibco-BRL) containing 1 mM sodium pyruvate (Whittaker Bioproducts) and 2 mM L-glutamine (Gibco-BRL), centrifuged and resuspended at $20 \times 10^6$ cells/ml in the same medium containing 0.1% human serum albumin (Alpha Therapeutics Corp., Los Angeles, Calif.). Cells were incubated with 10 ul of mAb/$10^6$ cells (between 0.5 and 20 ug mAb/$10^6$ cells) for 30 minutes at 4° C., washed once to remove excess antibody and resuspended in the same medium used in the mAb incubation. Magnetic goat anti-mouse IgG (Collaborative Biomedical Products, Becton Dickinson Labware, Bedford, Mass.) was added at a ratio of 20 magnetic particles/cell and the volume adjusted to give a final concentration of $2 \times 10^6$ cells/ml. Following incubation at 4° C. for 30 minutes, the antibody positive cells were removed using a strong magnet (Biomag separator, Advanced Magnetics, Inc., Cambridge, Mass.). The remaining cells were decanted, treated a second time with the magnet to remove any residual positive cells and the negative cells centrifuged and resuspended in AIM V medium with antibiotics containing 1 mM sodium pyruvate and 2 mM L-glutamine. The number of viable cells was determined using trypan blue exclusion and the cells used in proliferation assays or for cytokine production as detailed below.

7. Proliferation of EVA Cells in Response to PMA

Having established that phenotypically EVA cells were predominantly T lymphocytes, the functional activity of these cells in vitro was determined. Specifically, EVA cells were assayed for their ability to proliferate in response to PMA—a protein kinase C activator. PMA at 50–100 ng/ml has been shown to directly stimulate T-lymphocyte proliferation and at lower concentrations, typically 1–10 ng/ml, to enhance T-lymphocyte proliferation in response to mitogen or calcium ionophore stimulation.

EVA cells (obtained following overnight incubation at 4° C. in infusion medium, as detailed above in Section 3), from 15 patients, and the apheresis-derived PBMC (from which they were generated) or EVA cells depleted of CD8+ and/or CD4+ cells (as detailed above in Section 6) were centrifuged and resuspended in AIM V medium with antibiotics (Gibco-BRL, Grand Island, N.Y.) containing 1 mM sodium pyruvate (Whittaker Bioproducts, Walkersville, Md.) and 2 mM L-glutamine (Gibco-BRL, Grand Island, N.Y.). The cells were cultured at $1 \times 10^6$ viable cells/ml in 96 well flat-bottomed microtitre plates (Costar, Cambridge, Mass.) at 37° C. in a humidified 5% $CO_2$ incubator. PMA (Sigma Chemical Co., St. Louis, Mo.) at various concentrations was added at the start of the cultures. The PMA was dissolved in anhydrous ethyl alcohol (Fisher Scientific, Fair Lawn, N.J.) at a concentration of 100 ug/ml and stored at –40° C. prior to use. The cells were cultured for 46–48 hours and labelled with $1$uCi/well $^3$H-methyl-thymidine ($^3$H-TdR; New England Nuclear-Dupont, Boston, Mass.) during the last 6 hours. The cells were frozen and subsequently harvested onto glass fibre filters and the amount of radioactivity incorporated determined by liquid scintillation counting. The results are presented as the average counts/minute (cpm) obtained from triplicate determinations. Unless otherwise indicated, the concentration of PMA used to stimulate the cells for proliferation was 1 ng/ml.

The degree of activation of EVA cells in vitro was determined by measuring their ability to proliferate in response to PMA—a protein kinase C activator. PMA at 50–100 ng/ml has been shown to directly stimulate T-lymphocyte proliferation and at lower concentrations (typically 1–10 ng/ml) to enhance T-lymphocyte proliferation in response to mitogen or calcium ionophore stimulation. EVA cells from 15 patients, and the apheresis-derived PBMC from which they were generated, were stimulated for 48 hours with various concentrations of PMA and the results from three representative patients are shown in FIGS. 1A–1C. EVA cells showed substantial proliferation to both 1 and 10 ng/ml concentrations of PMA, with the optimal concentration being 1 ng/ml. Very little spontaneous proliferation was observed with EVA cells that were cultured in the absence of additional stimulation. In these experiments, the EVA cells were extensively washed to remove any residual stimulants and the cells stored overnight at 4° C. in infusion medium prior to their further stimulation with PMA. Therefore, PMA is being used as a probe to reveal the functional activity of these cells and not concurrently as a co-stimulant.

In marked contrast to the results obtained with EVA cells, apheresis-derived PBMC did not proliferate in response to PMA at the three doses tested (FIGS. 1A–1C). Additionally, culturing the apheresis-derived PBMC for five days in the absence of conditioned medium did not activate these cells to proliferate substantially following additional stimulation with 1 ng/ml PMA. These results demonstrate that EVA cells have actively acquired their enhanced capacity to respond to a low dose of PMA as a result of their prior stimulation with conditioned medium.

Proliferation of CD4+ and CD8+ cells in response to PMA

To further characterize which cells in the EVA cell populations were proliferating in response to PMA, EVA cells were depleted of CD4+ and/or CD8+ cells and the remaining cells stimulated for proliferation with PMA. Depletion rather than positive selection was used in these experiments to eliminate the possibility of activating the cells with mAb prior to their stimulation with PMA.

Apheresis-derived PBMC and EVA cells were cultured in 0.5 or 1 ml cultures at $1 \times 10^6$ viable cells/ml in 48 well tissue culture plates (Costar, Cambridge, Mass.) and stimulated with PMA essentially as detailed above for proliferation. Following 24–72 hours incubation, cell free supernatants were obtained and stored at –70° C. prior to assay.

As shown in FIG. 2A, depleting both CD4+ cells together with CD8+ cells from the same sample of EVA cells virtually eliminated the proliferation observed in response to PMA. Therefore, these two populations of cells account for essentially all of the proliferation observed in response to PMA and only a minimal amount of proliferation is contributed by the residual B cells, natural killer cells, or monocytes. EVA cells were also depleted of either CD4+ or CD8+ cells and the remaining cells, highly enriched for the non-depleted phenotype, stimulated with PMA (FIG. 2B). Both populations of depleted cells proliferated to virtually the same extent as the untreated cells (FIG. 2B), demonstrating that both CD4+ and CD8+ EVA cells proliferate in response to PMA.

Figure 3A:
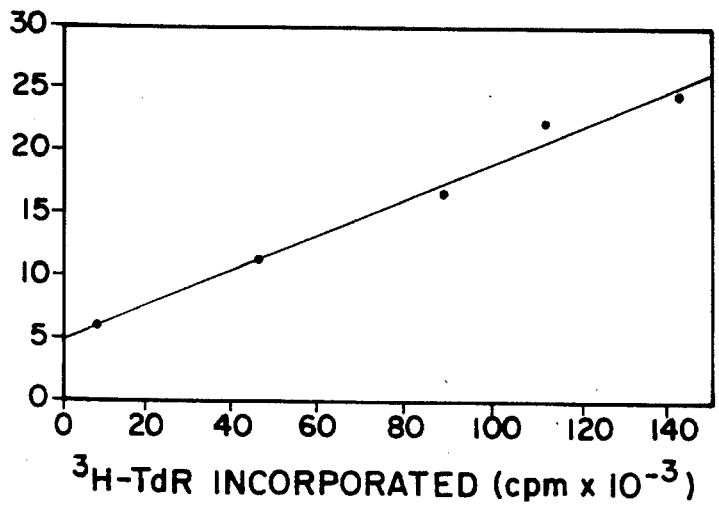
FIGS. 3A–3C are graphs showing the correlation of PMA-induced proliferation and CD25(IL-2R) expression within patients. Apheresis-derived PBMC from 3 different patients were stimulated with 0, 0.2, 1, 5, and 25 ng/ml OKT3 essentially as detailed for the generation of EVA cells as detailed in the Examples. The stimulated cells were then characterized for CD25(IL-2R) expression and were assayed for proliferation following additional stimulation at 37° C. for 48 hours with 1 ng/ml PMA. The percentage of CD25(IL-2R) positive cells from each of these cultures is plotted against the amount of $^3$H-TdR incorporated for that culture. Each successive point represents one culture stimulated with an increasing amount of OKT3. Each of FIGS. 3A, 3B and 3C represents a different patient's cells.
Figure 3B:
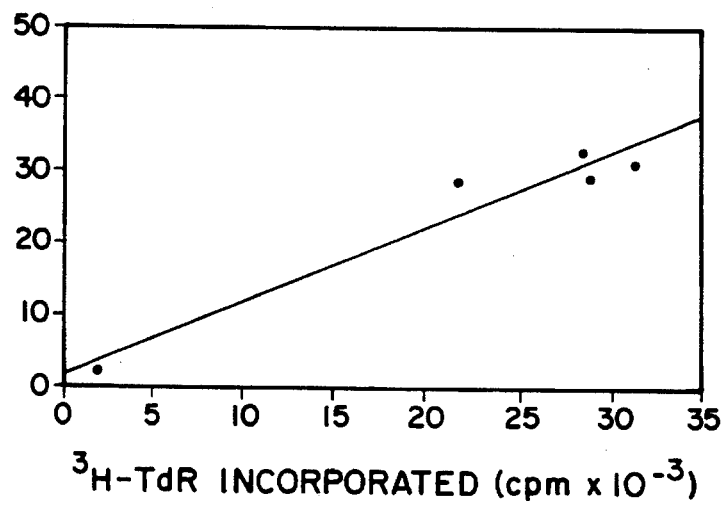
Figure 3C:
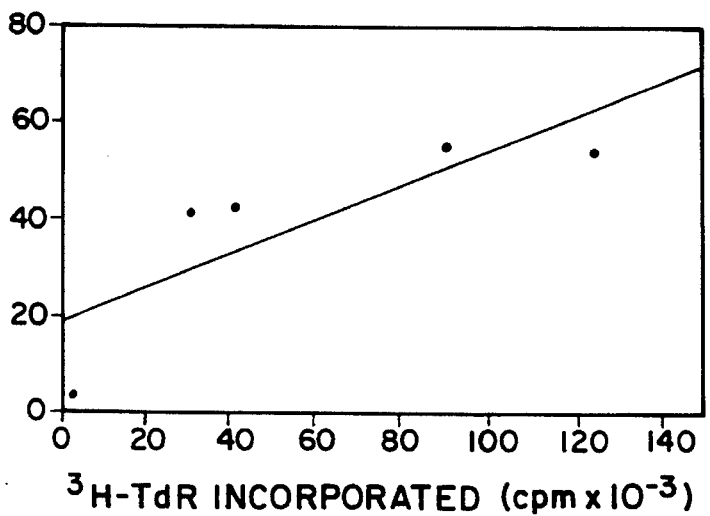

Proliferation in response to PMA correlates with CD25(IL-2R) expression within individual patient samples To determine whether the magnitude of the proliferative response to PMA could be correlated with CD25(IL-2R) expression, apheresis-derived PBMC from three patients were directly stimulated with various concentrations of OKT3, and the resulting cells assayed for the proportion of CD25(IL-2R)+ cells and for proliferation in response to PMA. CD25(IL-2R) expression is clearly established as a marker for activated human T cells. As shown in FIGS. 3A–3C, a strong correlation was observed between these two parameters within each of the three patients tested ($r^2$=0.99, 0.97 and 0.82, respectively). Therefore, within patients, CD25(IL+2R) expression and proliferation in response to PMA are related phenotypic and functional measures of the level of T cell activation. This correlation however did not extend interpatient.

c. Distribution of the proliferative response to PMA

The magnitude of the proliferative responses observed following PMA stimulation from over 90 mRCC patient EVA cell samples has been determined. Greater than 90% of these samples showed enhanced proliferation following further stimulation with PMA (defined as a minimum 3-fold increase in $^3$H-TdR incorporated compared to medium alone). In Table III, the proliferation results obtained were arbitrarily divided into three groups, based on the absolute amount of $^3$H-TdR incorporated. The range of responses observed varied from <2,000 cpm to >200,000 cpm of $^3$H-TdR incorporated, and "low" and "high" responders defined as incorporating <20,000 and >100,000 cpm of $^3$H-TdR. respectively. As shown in Table III, 41% of EVA cell samples were low responders and 22% were high responders.

TABLE III

Distribution of the proliferative responses of EVA cells following further stimulation with PMA

| | $^3$H-TdR incorporated (cpm) | | |
|---|---|---|---|
| | <20,000 | 20–100,000 | >100,000 |
| N* | 38 | 35 | 20 |
| % of total | 41 | 38 | 22 |

Figure 4A:
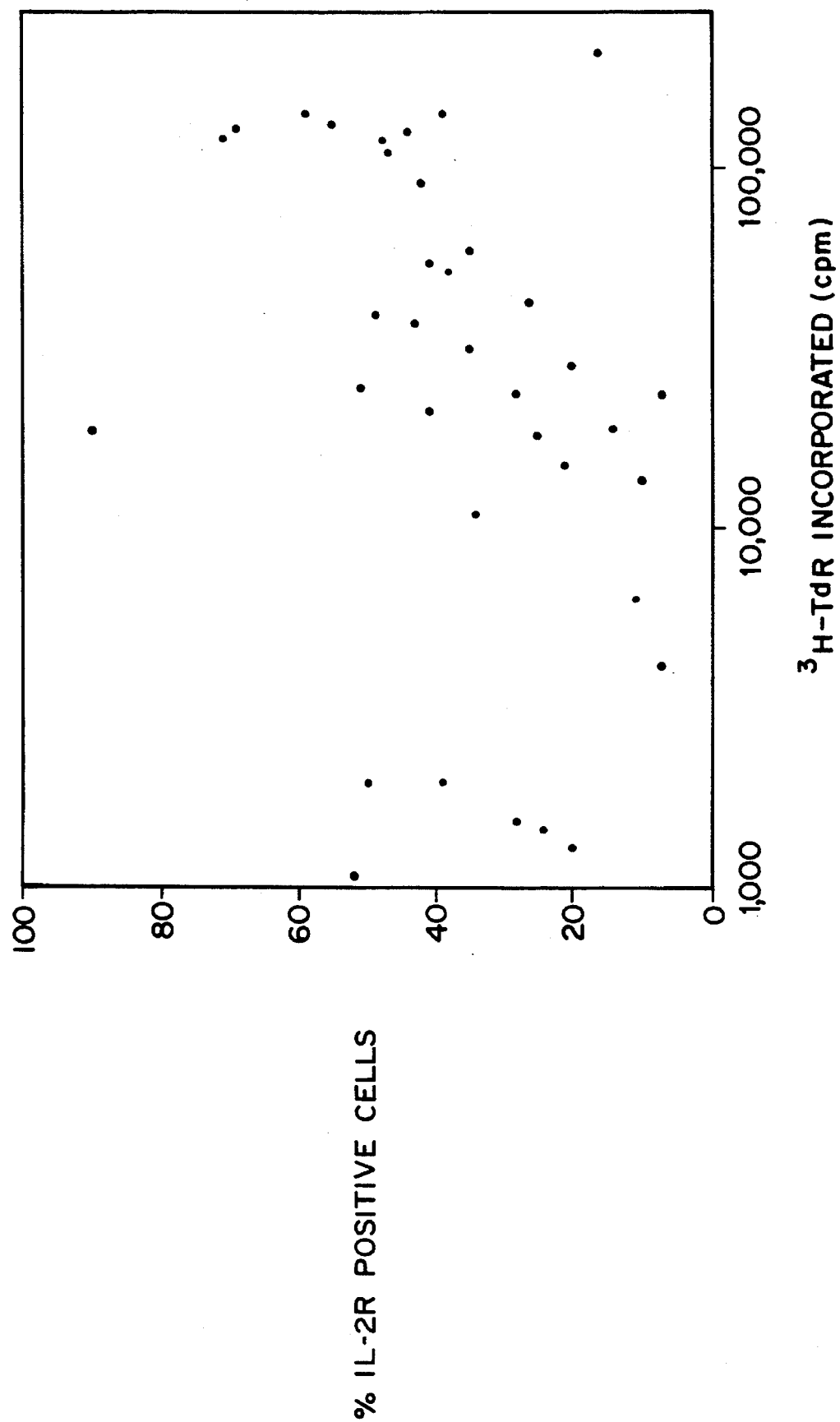
FIGS. 4A and 4B are graphs which show the lack of interpatient correlation between PMA-induced proliferation and either CD25(IL-2R) expression or CD45RO expression. EVA cell samples were characterized for both CD25(IL-2R) expression and CD45RO expression and were then assayed for proliferation following additional stimulation at 37° C. for 48 hours with 1 ng/ml PMA as described in the Examples.
Figure 4B:
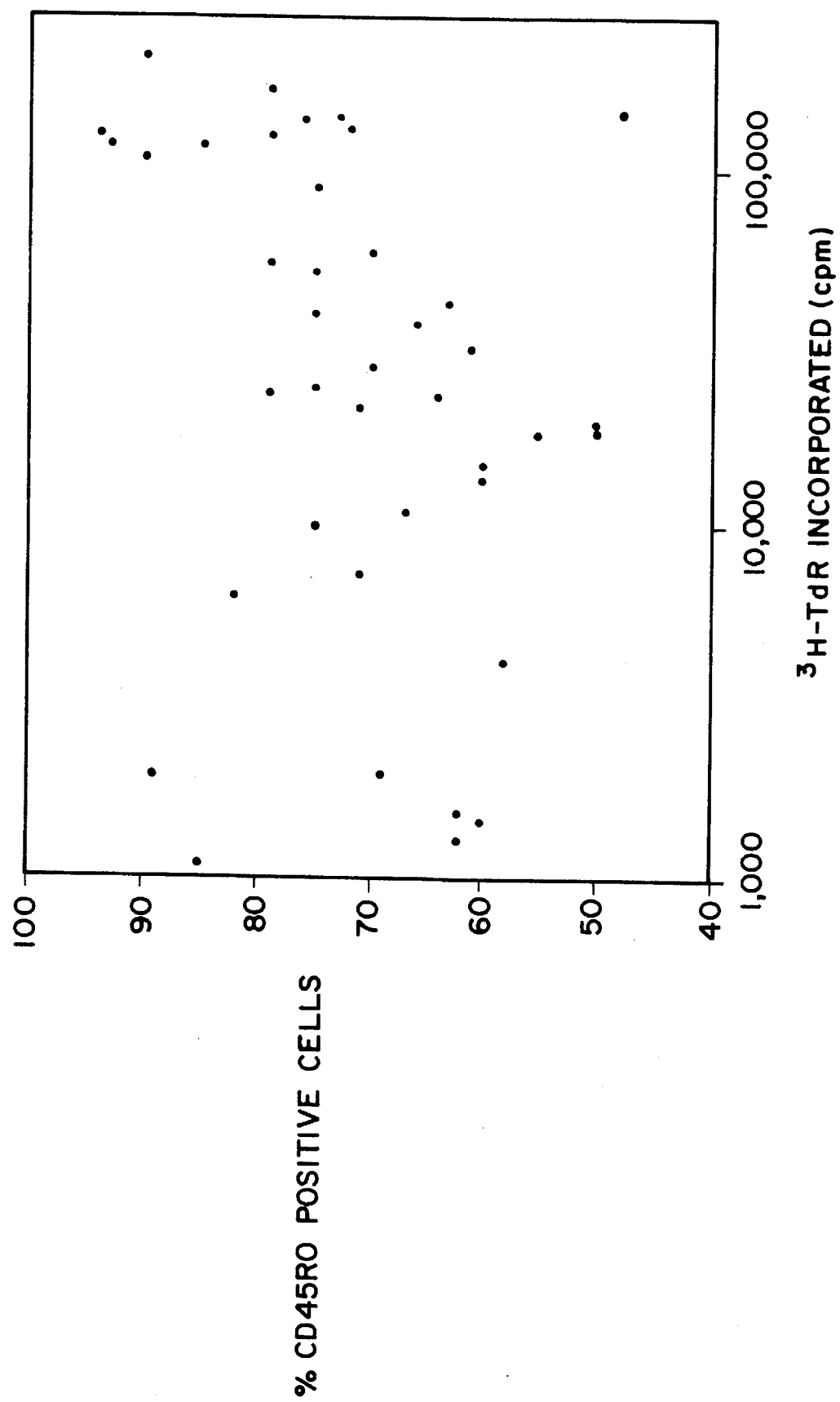

EVA cells were stimulated with 1 ng/ml PMA for 48 hours at 37° C. and labelled with $^3$H-TdR during the final 6 hours.
*Number of EVA cell samples d. Proliferation to PMA does not correlate with CD25(IL-2R) or CD45RO expression interpatient To determine whether the magnitude of proliferation observed following PMA stimulation could be directly related to CD25(IL-2R) expression between patients, the amount of $^3$H-TdR incorporated by individual EVA samples following further stimulation with PMA was plotted against the proportion of CD25(IL-2R)+ cells in that sample. As shown in FIG. 4A, there was little correlation between patients—EVA cells with comparable proportions of CD235(IL-2R)+ cells showed substantially different levels of proliferation in response to PMA. Similarly, the proportion of cells expressing the CD45RO cell surface marker associated with activated "memory" T cells also did not show a strong interpatient correlation with proliferation to PMA (FIG. 4B). These results may reflect the limitations in using only single phenotypic markers to accurately determine immunological responsiveness. Interestingly, those EVA samples that incorporated >100,000cpm of $^3$H-TdR in response to PMA had significantly higher percentages (p<0.05) of cells that were CD3+, CD25(IL-2R)+ and CD45RO+ than those EVA samples that incorporated <20,000cpm of $^3$H-TdR (Table IV). No significant differences were observed with the proportions of other cell types tested (Table IV). Therefore, poorly activated cultures are both phenotypically unactivated and functionally poor responders, while the converse is true for highly activated cultures.

TABLE IV

Phenotypes of EVA cells that had low versus high proliferative responses to

| | % Positive lymphocytes (mean ± SEM) | | |
|---|---|---|---|
| | Low responders* | High responders† | Difference (p$^§$) |
| CD3+ | 84 ± 2 | 92 ± 1 | <0.0086 |
| CD4+ | 63 ± 4 | 72 ± 2 | <0.056 |
| CD8+ | 21 ± 5 | 29 ± 4 | <0.22 |
| CD25 (IL-2R)+ | 24 ± 4 | 49 ± 4 | <0.0005 |
| CD3+ MHC Class II+ | 39 ± 5 | 44 ± 5 | <0.44 |
| CD45RA+ (naive) | 55 ± 3 | 50 ± 5 | <0.48 |
| CD45RO+ (memory) | 61 ± 3 | 81 ± 2 | <0.00007 |
| CD45RA+ CD45RO+ | 24 ± 2 | 25 ± 3 | <0.85 |

*Low responders (N = 11) incorporated <20,000 cpm $^3$H-TdR in response to PMA
†High responders (N = 10) incorporated >100,000 cpm $^3$H-TdR in response to PMA
§Values for p were calculated by use of the two-tailed Student's t test assuming variances.

e. Cytokine production by EVA cells in response to PMA

EVA cells were also evaluated for their ability to produce cytokines in response to PMA. Shown in FIGS. 5A–5C, 6A–6C, and 7A–7C are the results from three representative EVA cell samples from 15 samples analyzed. gIFN, GM-CSF and TNF-alpha were all produced following 48 hours stimulation with 1 or 10 ng/ml PMA. Relatively low or undetectable levels of all three of these cytokines were spontaneously produced from EVA cells cultured in medium alone or from EVA cell cultures stimulated with only 0.1 ng/ml PMA. The apheresis-derived PBMC used to generate these EVA cells o produced much less gIFN and GM-CSF in response to these three doses of PMA (open circles, FIGS. 5A–5C and 6A–6C), but did produce moderate levels of TNF-alpha (FIGS. 7A–7C). Therefore, as observed for proliferation, EVA cells show enhanced capability to produce cytokines in response to low doses of PMA and this enhanced ability is actively acquired in response to stimulation with conditioned medium.

8. In Vitro Assay for Measuring the Functional Activation Level of Immune Cells

One of the major challenges associated with adoptive immunotherapy is the identification of in vitro assays that are useful in predicting in vivo efficacy. ALT is based predominantly on the infusion of activated T lymphocytes, and therefore accurate measurement of the level of T cell activation is an important first step in correlating in vitro and in vivo responses.

The treatment of mRCC patients with autologous immune cells activated in vitro with a combination of autologous cytokines and OKT3 has shown promising results in a randomized, controlled clinical trial. The EVA cells infused into these patients have been characterized phenotypically and functionally to begin to identify those properties that are important for their therapeutic efficacy.

The EVA cells used in this therapy were activated by conditioned medium consisting of autologous cytokines and OKT3. This combination of stimulants results in the rapid and synergistic activation of the T cells in these cultures, while reducing the amount of OKT3 that remains associated with the cells. The EVA cells resulting from conditioned medium stimulation were predominantly T lymphocytes comprised of substantial proportions of both CD4+ and CD8+ cells. These T cells expressed high proportions of the early and late activation markers CD25(IL-2R) and MHC class II antigens. Both of these markers are directly related to the potential functional activity of these cells. CD25(IL-2R)+ cells can proliferate in response to IL-2 and MHC class II+ T cells can efficiently present processed antigens to other T cells along with necessary co-stimulatory signals.

EVA cell samples also contained a high proportion of CD45RO+ cells. The CD45 glycoprotein is a tyrosine-specific phosphatase proposed to play an important role in T cell activation mediated through the T cell receptor. The expression of the CD45RO low molecular weight isoform is associated with both more efficient signal transduction and the differentiation of "naive" T cells into "memory" cells in response to a productive antigen stimulation. "Memory" T cells, by definition, are responsible for the enhanced secondary immune responses observed to recall antigens, and presumably would also have enhanced responses to tumor-associated antigens. Therefore, it may be advantageous that EVA cell samples contain a large proportion of these cells (greater than 80% in many cases), which should have this reduced requirement for their further activation. Additionally, CD45RO+ cells have been demonstrated to have distinct recirculation patterns in vivo and may therefore be able to efficiently target to inflammatory sites containing tumor cells. EVA cells also contained a significant level of CD45RA+ cells. Recently, it was suggested that CD45RA+ and CD45RO+ cells could synergize during T cell activation as these different populations of cells produce and respond to complimentary cytokines. This observation and the demonstrations that subpopulations of CD8+ cells can be functionally activated and still retain expression of CD45RA suggest that heterogeneity in terms of both CD45RO+ and CD45RA+ cells may be an important characteristic of EVA cells.

Having established by phenotypic markers that EVA cells are predominantly activated T cells, the inventors reasoned that an accurate, overall measure of the functional activation level of these cells would be a good starting point in correlating in vitro activity with in vivo potency. This invention is directed to an assay that measures the immunological reactivity of these cells in vitro. The EVA cells were characterized for their ability to proliferate and produce cytokines in response to PMA. PMA is a potent, protein kinase C activator that has been used in a variety of T cell activation studies as a "second signal." As PMA activity is independent of accessory cells, the use of PMA eliminates the difficulties associated with accurately measuring T cell activation in cultures with varying or low amounts of accessory cells. In addition, PMA does not require cell surface receptor crosslinking for its co-stimulatory effects.

Most of the previous work on PMA has involved the simultaneous exposure of purified T cells to PMA and an additional stimulant, typically ionomycin, PHA or Con A. The inventors have taken an alternative approach and added PMA to cells that had been previously activated with conditioned medium, then extensively washed to remove any remaining stimulants and stored overnight at 4° C. The inventors presumed that, as a result of their prior activation, these cells would be able to respond to further stimulation with PMA alone. The results demonstrate that EVA cells, but not the apheresis-derived PBMC from which they were generated, proliferated and produced cytokines following further stimulation with a low dose of PMA. Therefore, as a result of their activation with conditioned medium, EVA cells have acquired an increased sensitivity (i.e., are "primed" to respond) to further stimulation with this classical "second signal" stimulant. Furthermore, these results, along with the variation in the magnitude of the proliferative responses of different EVA cell samples to PMA and the strong correlation, within patients, between CD24(IL-2R)+ cells and PMA-induced proliferation suggest that PMA can be used as a probe to quantitatively measure the functional activation level of these cells.

Within the EVA cells, depletion experiments revealed that essentially all of the proliferation observed in response to PMA resulted from the T lymphocytes in these cultures. Depleted cultures consisting predominantly of B cells, natural killer cells and monocytes did not proliferate substantially following further stimulation with PMA, a result that is consistent with the original cultures having been activated with a stimulant that does not efficiently stimulate these cell types. Depletion experiments also revealed that both CD4+ and CDS+ cells were primed to proliferate in response to PMA.

The relationship between PMA responsiveness and overall activation level was strongly supported by the correlation, within patients, of the magnitude of proliferation induced by PMA and the proportion of cells expressing CD25(IL-2R)—a classical cell surface marker for human T cell activation. This correlation did not extend interpatient, which may reflect the limitations in using a single phenotypic marker to accurately determine overall immunological responsiveness between patients. It is also possible that the EVA cells that proliferate in response to PMA are not exclusively CD25(IL- 2R)+. It is known, for example, that PMA and other tumor promoters can stimulate T cell proliferation in an IL-2 independent manner. Similarly, PMA responsiveness did not show a strong interpatient correlation with the proportion of cells that were CD45RO+. However, a comparison of low versus high responders to PMA did show a statistically significant increase in both CD45RO+ cells and CD25(IL-2R)+ cells in the high responders. A possible explanation for these results is that high proportions of CD45RO+ and CD25(IL-2R)+ cells are present in cultures that were in fact activated at some point during their generation, but at the time of assay had lost to a variable degree their ability to proliferate following further stimulation. As a result, variable proportions of phenotypically activated but functionally non-responsive cells would be present in the low PMA responders resulting in only a poor correlation with PMA responsiveness. Therefore, measuring the functional ability of these cells using PMA may more accurately reveal the overall immunological capabilities of these cells than the expression of these markers.

Over 90 mRCC patient EVA cell samples have been analyzed. Greater than 90% of these samples showed a significant proliferative response following further stimulation with PMA. However, the magnitude of the proliferative responses observed varied substantially among these different samples indicating quantitative differences in their level of activation or priming. Upon infusion into patients, these EVA cell samples will have quantitative differences in their ability to function in response to the various immunological signals that they would encounter. PMA responsiveness can therefore predict EVA cell potency and can be used to optimize the generation of these and other activated cells used in adoptive immunotherapy.

9. Proliferative Responses of EVA Cells to Calcium Ionophore-Ionomycin

Figures 8A, 8B, 8C:
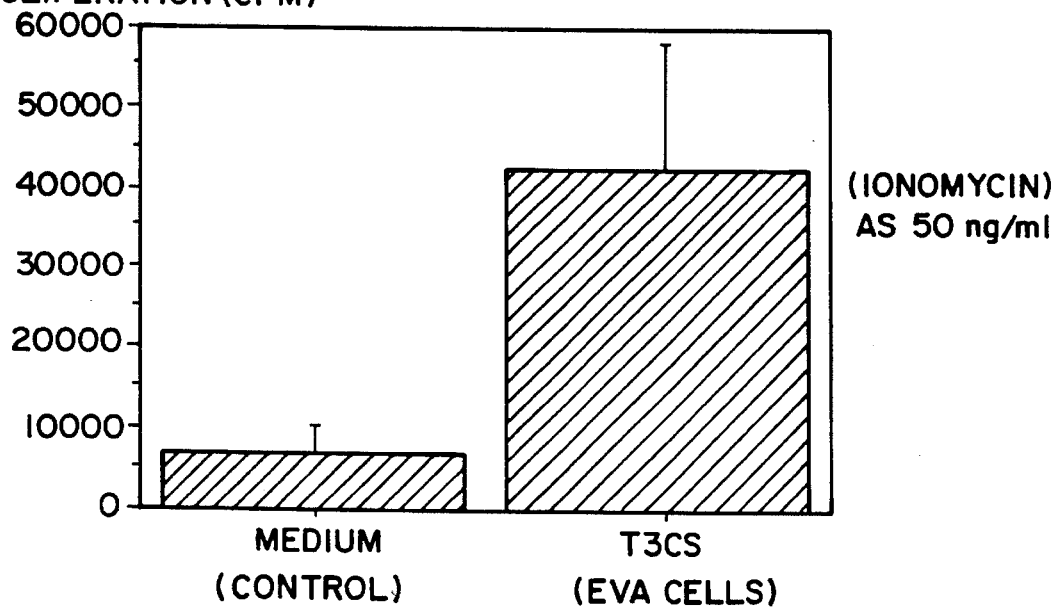
FIG. 8 is a bar graph showing the enhancement of ionomycin responses by prior in vitro activation of lymphocytes from mRCC patients with autologous T3CS, the conditioned medium of cytokine and OKT3.

Another stimulant that may be used in the in in vitro assay is a calcium ionophore such as ionomycin as a probe for the assessment of T cell activation. PBMC from eight mRCC patients were stimulated in the culture with either 25% autologous T3CS or medium alone (control) for 5 days following the EVA cell generation protocol described above. After storage overnight, EVA cells or the control cells were tested for their ability to proliferate in response to ionomycin. The cells were seeded 1 million cells/ml in AIM V medium in 96-well flat-bottom culture plate with or without 50 ng/ml ionomycin, and cultured in a humidified 37° C. incubator with 5% CO2 for 48 hours. The cells were pulsed with tritiated thymidine during the last 6 hours of culture and were then harvested to determine the radioactivity incorporation by liquid scintillation counting. Table V is a table showing a comparison between ionomycin-stimulated proliferation of resting and nonresting immune cells. "Medium" refers to resting cells, previously cultured under non-activating conditions, and "T3CS" refers to EVA cells activated by culture with cytokine-containing T3CS. Cell proliferation was determined by measuring cpm of tritiated thymidine incorporated into cultures derived from cells of 8 renal cell carcinoma patients. Table VI is a table showing statistical calculation of significant difference (p=0.0245) between the ionomycin-stimulated proliferation of resting and nonresting cells. As shown in Table V, VI and FIG. 8, EVA cells demonstrated a significant enhancement (4.1 fold greater) in cell proliferation compared to control cells in response to ionomycin. These results indicate that ionomycin, similar to PMA, can be used as an direct activation probe to quantitate the degree of activation of immune cells.

Although the foregoing invention has been described in some detail by way of illustration and example for purposes of clarity of understanding, it will be obvious to one skilled in the art that certain changes and modifications may be practiced within the scope of the invention, as limited only by the scope of the appended claims.

What is claimed is:

1. A method for detecting a primed state of activation of ex-vivo activated (EVA) immune cells comprising:

(a) providing a sample of EVA immune cells;

(b) contacting the EVA immune cells with a single, intracellular-acting stimulant, wherein said stimulant at the dose used for stimulation will effectively stimulate primed immune cells to activity but wherein said stimulant does not effectively stimulate resting immune cells to activity;

(c) measuring the activity of the EVA immune cells that were effectively stimulated by said stimulant;

(d) contacting a sample of apheresis-derived peripheral blood mononuclear cells with said stimulant, wherein said stimulant at the dose used for stimulation will effectively stimulate primed immune cells to activity but wherein said stimulant does not effectively stimulate resting immune cells to activity;

(e) measuring the activity of the peripheral blood mononuclear cells that were effectively stimulated by said stimulant; and (f) comparing the level of activity of the EVA immune cells with the level of activity of the peripheral blood mononuclear cells, wherein an increase in said level of activity of said EVA immune cells compared to said peripheral blood mononuclear cells indicates that said EVA immune cells are in a primed state of activation.

2. The method of claim 1 wherein said stimulant is a protein kinase C activator.

3. The method of claim 2 wherein said protein kinase C activator is 1,2-dioctanoylglycerol.

4. The method of claim 2 wherein said activator is a phorbol ester.

5. The method of claim 4 wherein said phorbol ester is selected from the group consisting of phorbol myristate acetate and phorbol dibutyrate.

6. The method of claim 1 wherein said stimulant is a tumor promoter.

7. The method of claim 6 wherein said tumor promoter is selected from the group consisting of teleocidin and 3-methyl-cholanthrene.

8. The method of claim 1 wherein said stimulant is a calcium ionophore.

9. The method of claim 8 wherein said calcium ionophore is selected from the group consisting of ionomycin and calcimycin.

10. The method of claim 1 wherein said activity is cell proliferation.

11. The method of claim 1 wherein said activity is cell cytokine production.

12. The method of claim 1 wherein said activity is production of chemotactic factors.

13. A method for predicting clinical efficacy of immunotherapy of a patient with a sample of EVA immune cells in a primed state derived from said patient comprising:

(a) contacting a portion of said sample of EVA immune cells with a single, intracellular-acting stimulant, wherein said stimulant at the dose used for stimulation will effectively stimulate primed immune cells to activity but wherein said stimulant does not effectively stimulate resting immune cells to activity; and, (b) measuring the activity of said EVA immune cells following stimulation;

(c) contacting a sample of apheresis-derived peripheral blood mononuclear cells derived from said patient with said stimulant;

(d) measuring the activity of said peripheral blood mononuclear cells; and (e) comparing the level of activity of the EVA immune cells with the level of activity of said peripheral blood mononuclear cells, wherein an increase in said level of activity of said EVA immune cells compared to said peripheral blood mononuclear cells indicates clinical efficacy of immunotherapy of said patient with said sample of EVA immune cells.

14. The method of claim 13 wherein said stimulant is a protein kinase C activator.

15. The method of claim 14 wherein said protein kinase C activator is 1,2-dioctanoylglycerol.

16. The method of claim 14 wherein said activator is a phorbol ester.

17. The method of claim 16 wherein said phorbol ester is selected from the group consisting of phorbol myristate acetate and phorbol dibutyrate.

18. The method of claim 13 wherein said stimulant is a tumor promoter.

19. The method of claim 18 wherein said tumor promoter is selected from the group consisting of teleocidin and 3-methyl-cholanthrene.

20. The method of claim 13 wherein said stimulant is a calcium ionophore.

21. The method of claim 20 wherein said calcium ionophore is selected from the group consisting of ionomycin and calcimycin.

22. The method of claim 13 wherein said activity is cell proliferation.

23. The method of claim 13 wherein said activity is cell cytokine production.

24. The method of claim 13 wherein said activity is immunoglobulin production.

25. The method of claim 13 wherein said activity is production of chemotactic factors.

26. An assay to measure degree of activation of EVA immune cells in a primed state prior to reinfusion into a patient for adoptive immunotherapy comprising:
   (a) contacting said EVA immune cells with a single, intracellular-acting stimulant,
   wherein said stimulant at the dose used for stimulation will effectively stimulate primed immune cells to activity but wherein said stimulant does not effectively stimulate resting immune cells to activity; and,
   (b) measuring the degree of activation of the stimulated EVA immune cells; and
   (c) ascertaining whether the degree of activation of said stimulated EVA immune cells is predictive of in vivo efficacy for the patient prior to reinfusion of the EVA immune cells into the patient.

27. The assay of claim 26 further comprising:
   (d) modifying said immunotherapy based upon the degree of activation of said EVA immune cells.

28. The assay of claim 26 wherein said immunotherapy is modified by restimulating said EVA immune cells.

29. The assay of claim 26 wherein said immunotherapy is modified by replacing said EVA immune cells.

30. The assay of claim 26 wherein said immunotherapy is modified by regulating the number of said EVA immune cells for reinfusion.

31. The method of claim 26 wherein said stimulant is a protein kinase C activator.

32. The method of claim 31 wherein said protein kinase C activator is 1,2-dioctanoylglycerol.

33. The method of claim 31 wherein said activator is a phorbol ester.

34. The method of claim 33 wherein said phorbol ester is selected from the group consisting of phorbol myristate acetate and phorbol dibutyrate.

35. The method of claim 26 wherein said stimulant is a tumor promoter.

36. The method of claim 35 wherein said tumor promoter is selected from the group consisting of teleocidin and 3-methyl-cholanthrene.

37. The method of claim 26 wherein said stimulant is a calcium ionophore.

38. The method of claim 37 wherein said calcium ionophore is selected from the group consisting of ionomycin and calcimycin.

39. The assay of claim 26 wherein said activity is cell proliferation.

40. The assay of claim 26 wherein said activity is cell cytokine production.

41. The assay of claim 26 wherein said activity is production of chemotactic factors.

42. A method for measuring the ability of EVA immune cells in a primed state to enhance the activity of resting immune cells comprising:
   (a) culturing a mixture of resting immune cells and EVA immune cells;
   (b) stimulating the mixture to activity with a single, intracellular-acting stimulant;
   wherein said stimulant at the dose used for stimulation will effectively stimulate primed immune cells to activity but wherein said stimulant does not effectively stimulate resting immune cells to activity; and,
   (c) measuring the activity of said mixture following stimulation, wherein an increase in the activity of said mixture compared to the activity of resting immune cells in the absence of EVA cells indicates that said EVA cells enhance the activity of said resting immune cells.

43. An assay to measure degree of activation of EVA immune cells in a primed state prior to reinfusion into a patient for adoptive immunotherapy comprising:
   (a) stimulating EVA immune cells to activity with a single, intracellular-acting stimulant to produce stimulated EVA immune cells,
   wherein said stimulant at the dose used for stimulation will effectively stimulate the primed immune cells to activity but wherein said stimulant does not effectively stimulate resting immune cells to activity; and,
   (b) measuring the degree of activation of the stimulated EVA immune cells, and
   (c) comparing the degree of activation of said stimulated EVA immune cells to a minimum standard to predict whether infusion of the EVA cells into the patient will be efficacious.

44. A method of assessing the immune cell status of a patient, wherein the immune cells are obtained from the patient comprising:
   (a) obtaining a sample of immune cells from the patient;
   (b) stimulating the immune cells to activity with a single, intracellular-acting stimulant;
   wherein said stimulant at the dose used for stimulation will effectively stimulate primed immune cells to activity but wherein said stimulant does not effectively stimulate resting immune cells to activity;
   (c) measuring the activity of said immune cells following stimulation; and
   (d) comparing said activity to a minimum standard as an indication of the immune status of a patient undergoing treatment with EVA cells.

* * * * *